United States Patent [19]

Iwasaki et al.

[11] Patent Number: 5,156,144
[45] Date of Patent: Oct. 20, 1992

[54] ULTRASONIC WAVE THERAPEUTIC DEVICE

[75] Inventors: Seiji Iwasaki; Naoki Uchiyama; Naomi Sekino, all of Hachioji, Japan

[73] Assignee: Olympus Optical Co., Ltd., Tokyo, Japan

[21] Appl. No.: 574,013

[22] Filed: Aug. 28, 1990

[30] Foreign Application Priority Data

| Oct. 20, 1989 | [JP] | Japan | 1-272981 |
| Oct. 20, 1989 | [JP] | Japan | 1-272982 |
| Oct. 20, 1989 | [JP] | Japan | 1-272984 |
| Oct. 31, 1989 | [JP] | Japan | 1-283767 |
| Jul. 2, 1990 | [JP] | Japan | 2-175576 |

[51] Int. Cl.$^5$ .................................. A61B 17/22
[52] U.S. Cl. .................. 128/24 EL; 128/660.03; 367/155
[58] Field of Search ......... 128/24 EL, 660.01, 660.03; 606/127, 128; 73/642, 625; 367/140, 157, 153, 155, 174, 175

[56] References Cited

U.S. PATENT DOCUMENTS 4,697,588 10/1987 Reichenberger .............. 128/24 EL
4,869,239 9/1989 Krauss et al. ................. 128/24 EL

FOREIGN PATENT DOCUMENTS

| 3501838 | 7/1986 | Fed. Rep. of Germany ... 128/24 EL |
| 60-214211 | 10/1985 | Japan . |
| 61-51511 | 3/1986 | Japan . |
| 61-154658 | 7/1986 | Japan . |
| 61-170446 | 8/1986 | Japan . |
| 1393489 | 5/1988 | U.S.S.R. ........................ 128/24 EL |

Primary Examiner—Kyle L. Howell
Assistant Examiner—Scott R. Akers
Attorney, Agent, or Firm—Armstrong & Kubovcik

[57] ABSTRACT

An ultrasonic wave curing device according to the present invention, can set the optimum ultrasonic wave focusing condition for curing, by using at least one of an ultrasonic wave oscillator, a conical reflector having a conical reflecting surface to reflect an ultrasonic wave, which comes from the ultrasonic wave oscillator, and a reflecting case having a concave, reflecting surface to focus to a position to be cured, an ultrasonic wave which is reflected, again, by the reflecting surface, after it is reflected by conical reflecting surfaces that are arranged around the periphery of the conical reflector.

11 Claims, 24 Drawing Sheets

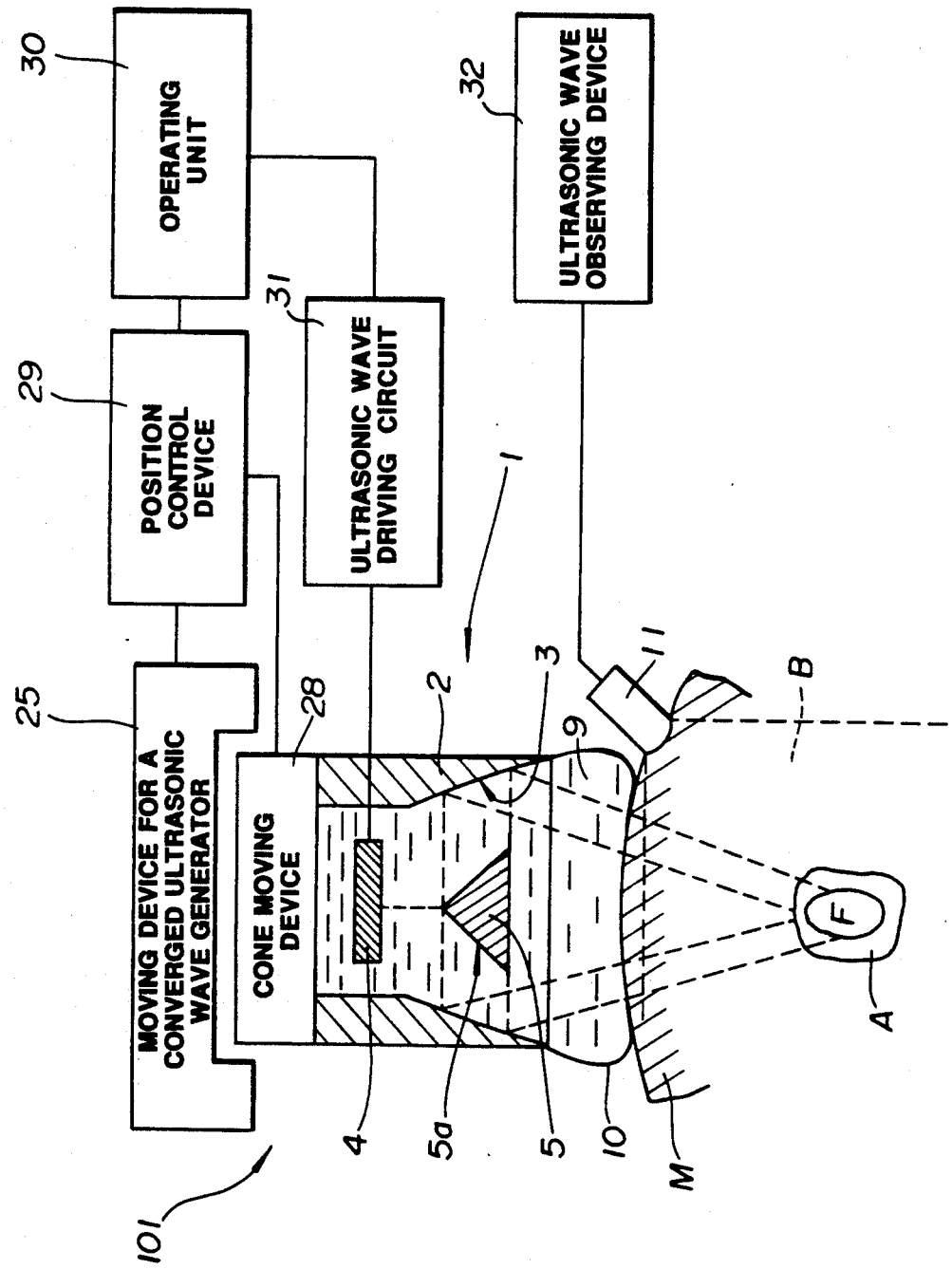

ULTRASONIC WAVE THERAPEUTIC DEVICE

BACKGROUND OF THE INVENTION

1. Field of the Invention

This invention relates an ultrasonic wave therapeutic device, more particularly a device for therapeutically treating tumors, calculi and so on, in which an ultrasonic wave generated outside the body is converged on an object having the tumors, calculi etc. inside the body.

2. Related Art Statement

As described on page 173 to 174 (Convergency of ultrasonic Waves) of the Handbook of Ultrasonic Wave Technology, on rotating parabolic surface reflector (called paraboloid reflector hereafter) and a reflector of straight cone of 90 degrees, are coupled; an ultrasonic wave incident on the straight cone reflector is reflected in all of the horizontal directions, as a cylindrical wave; then, the ultrasonic wave is reflected, again, by using a paraboloidal reflector so as to converge it on the focus. Such a device is known as a parabolic concentrator, and was disclosed by A Barome in 1952.

Japanese patent laid open No. 1985-214211 discloses an ultrasonic converging device, in which a conical horn of acute, top angle is arranged on the same axis as that of a horn having a paraboloidal surface so that the device is made small. And, Japanese patent laid open No. 1986-51511 discloses an ultrasonic wave converging device with a horn, in which an aperture of an end of ultrasonic wave transmitting and receiving elements is formed smaller than that of their front surfaces. Moreover, Japanese patent laid open No. 1986-170446 shows, as a shock wave generator, a device having a conical reflector and a reflector of inner paraboloidal reflecting surface, which is arranged on the common focus area, and any one of the above described reflectors can be replaced. Japanese patent laid open No. 1986-154658 proposes a shock wave tube having a conical reflector and a casing of inner paraboloidal reflecting surface, both of which move along the central axis of a shock wave generating means so as to change the focus of ultrasonic waves.

When the above described ultrasonic wave converging device is used for medical treatment, a converged situation of ultrasonic waves should be changed adequately depending on the condition of the object to be treated, because sizes and shapes of a tumor and a calculus are different for each individual patient.

However, in the above described prior art, it is necessary to move the ultrasonic wave generator itself in order to change the position of ultrasonic waves to be converged; thus, the ultrasonic wave cannot be focused on the object to be treated, a wide area cannot be treated at one time, and shock wave strength and its distribution cannot be changed at the focus of converged ultrasonic waves. Therefore a desired focusing condition of the ultrasonic wave cannot be obtained in accordance with a situation of objects to be treated.

OBJECT AND SUMMARY OF THE INVENTION

An object of the present invention is to supply an ultrasonic wave therapeutic device which has a simple construction, and in which an ultrasonic wave can be made to a suitable focusing condition depending on a position to be treated.

Another object of the present invention is to supply an ultrasonic wave therapeutic device, in which a focusing area of ultrasonic waves can be changed continuously by simple operation.

Still another object of the present invention is to supply an ultrasonic therapeutic device, in which shock wave strength and the strength distribution can be changed at the focus.

One more object of the present invention is to supply an ultrasonic wave therapeutic device, in which energy of ultrasonic waves can be supplied uniformly to an object to be treated depending on its size.

An ultrasonic wave therapeutic device according to the present invention comprises an ultrasonic wave generator to generate and irradiate a therapeutic ultrasonic wave; a conical reflector having a conical, reflecting surface which is arranged opposite to the ultrasonic wave irradiating surface of the ultrasonic wave generator an reflects and ultrasonic wave when it comes from the above described irradiating surface; and a concave reflecting case which is arranged around the periphery of said conical reflector, and reflects, again, an ultrasonic wave after it is reflected from said conical reflector. In this case, at least one reflecting surface of said conical reflector and said reflecting case is set to obtain two or more focusing positions of ultrasonic waves.

And, in the ultrasonic therapeutic device according to the present invention, a position of said conical reflector can be changed.

Moreover, an ultrasonic wave therapeutic device according to the present invention not only generates and irradiates an ultrasonic wave for medical treatment, but comprises an ultrasonic wave generator which is set to obtain a plurality of focusing positions of ultrasonic waves; a conical reflector having a mainly conical reflecting surface, which is arranged opposite to an ultrasonic irradiating surface of the ultrasonic wave generator so as to reflect the ultrasonic wave coming from said irradiating surface; and a concave reflecting mirror which is arranged around the periphery of said conical reflector, and concave reflects, again, an ultrasonic wave after it is reflected from the conical reflecting surface of the conical reflector so as to converge it on a position to be treated.

Other features and advantages of the present invention will be sufficiently made clear referring to the following description.

BRIEF DESCRIPTION OF THE DRAWINGS

FIG. 15 is a schematic constructional diagram of the seventh embodiment of the ultrasonic wave therapeutic device according to the present invention.

FIG. 23 shows a schematic cross sectional view of the ultrasonic wave therapeutic device, and FIGS. 24 (A) to (D) are diagrams showing the focusing conditions of ultrasonic waves.

DETAILED DESCRIPTION OF THE PREFERRED EMBODIMENTS

Figure 1:
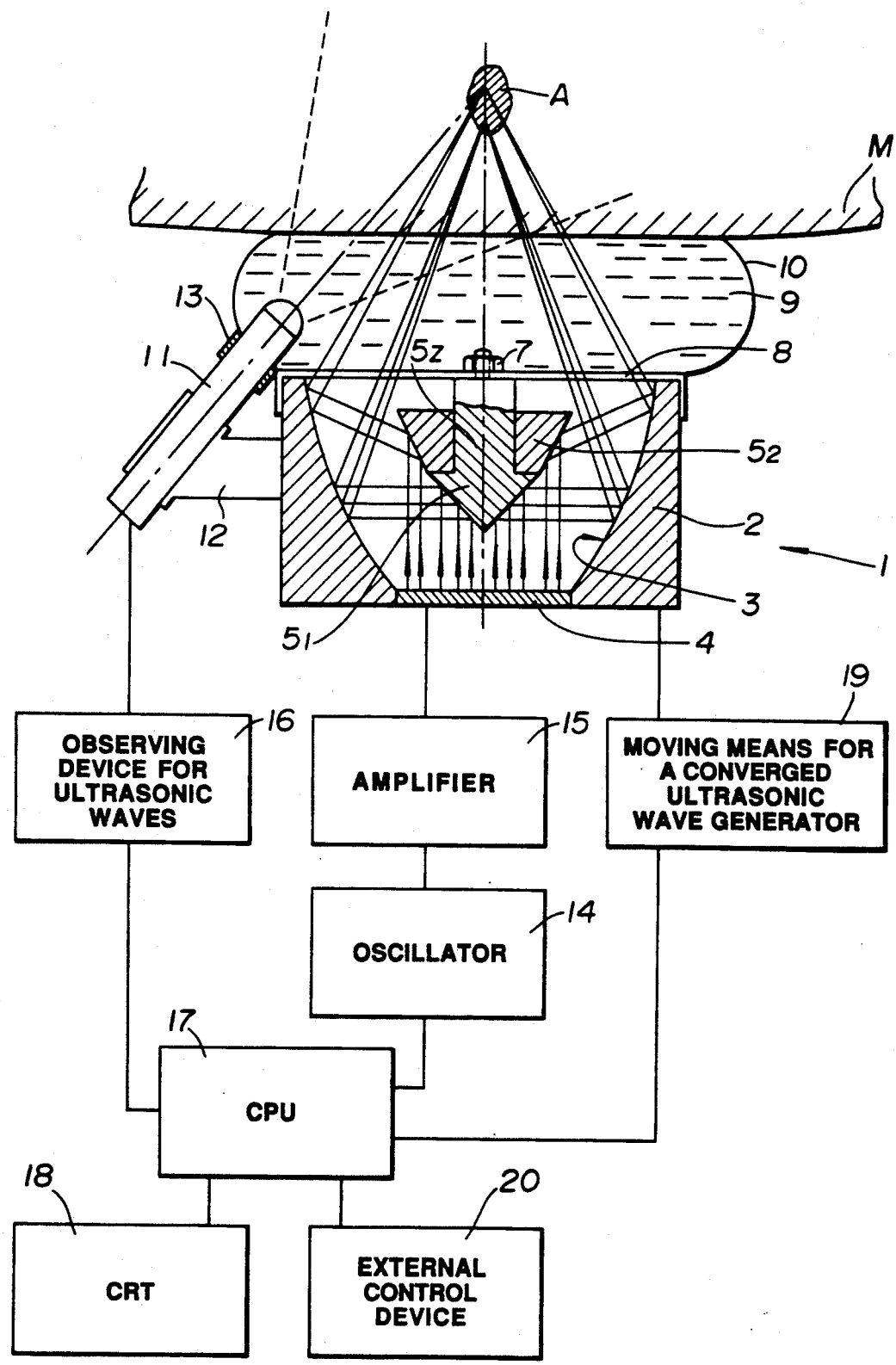
FIG. 1 is a schematic constructional diagram of the first embodiment of an ultrasonic wave therapeutic device according to the present invention.

FIG. 1 is a schematic constructional diagram of the first embodiment of an ultrasonic wave therapeutic device according to the present invention. The main part of a focused ultrasonic wave generator 1 is constructed with a concave, paraboloidal reflecting case 2, conical reflectors $5_1$ and $5_2$ which are arranged in the concave reflecting case 2, and an ultrasonic wave generator 4.

On the inner surface of the paraboloidal reflecting case 2 is formed a paraboloidal reflecting surface 3, the lower part of which is equipped with, for example a piezoelectric element of PZT or a Langeban oscillator tightened with bolts on the central axis of the reflecting surface. The ultrasonic wave generator 4 is provided for generating a therapeutic ultrasonic wave and irradiating it toward the conical reflectors $5_1$ and $5_2$. Opposite to the ultrasonic wave irradiating surface of the wave generator 4, the conical reflectors $5_1$ and $5_2$ are arranged on the central axis of the reflecting case 2, as will be described in the following.

In this embodiment, the conical reflector consists of a first conical reflecting body $5_1$ of straight cone and a second conical reflecting body having a different top angle from that of the first reflecting body $5_1$. The front end of a supporting axis $5_2$ which is constructed as one body with the first conical reflecting body, is fixed to a cone fixing bar 8 which is mounted on the upper reflecting surface of the reflecting case 2, by using a nut 7; such that the first conical reflecting body $5_1$ is supported, and the second conical reflecting body $5_2$ is arranged with the first reflecting body $5_1$, and its central axis is pierced by the supporting axis $5_1$.

In order to focus an ultrasonic wave coming from the ultrasonic wave generator 1 on a tumor A of the human body M effectively, a water bag 10 is arranged between the upper aperture of the paraboloidal reflecting case 2 and a surface of the human body M. The water bag 10 is constructed, for example, with a vessel in which an ultrasonic wave transmitting liquid 9 is filled. The liquid can be water, from which air is removed. The water bag is mounted to cover the upper aperture of the reflecting case 2. An ultrasonic wave observing probe 11 is mounted on one side of the reflecting case 2, by using a probe fixing means 12, so as to observe the position, size; etc. of the tumor to be cured in the human body M. The front end of the ultrasonic wave observing probe 11 is inserted into the water bag 10 in order to observe tumors and the like more accurately. The gap between the water bag 10 and the ultrasonic wave observing probe 11 is kept water-tight by using a rubber band 13 etc.

The above described, ultrasonic wave generator 4 is supplied with a driving signal, which is obtained by amplifying an output signal by amplifier 15 after it is generated from an oscillator 14. An observing output of the ultrasonic wave observing probe 11 is processed by an ultrasonic wave observing device 16, and monitored on the displaying device 18, for example on a CRT, through the CPU (central processing unit) 17. On the other hand, in order to adjust the focusing position of the ultrasonic wave to a position to be treated, for example the tumor A, the above described, focused ultrasonic wave generator 1 should be moved. Thus, a moving means of the focused ultrasonic wave generator 19 is driven by using an external control device 20, for example a keyboard, through the CPU 17, and therefore the position of the focused ultrasonic wave generator 1 is controlled.

The function of the, ultrasonic wave therapeutic device according to the first embodiment will next be described. At first, a surgeon observes by using the displaying device 18 such as CRT, a video output signal of the ultrasonic wave observing device 16, the signal being detected from a position to be treated, for example tumors, etc. in the human body M, by using the ultrasonic wave observing probe 11. The first and second conical reflectors $5_1$ and $5_2$, or at least two reflectors which have the optimum reflecting surface, are selected among a plurality of conical reflectors having a top angle which differs depending on the size of the position to be treated, the reflectors being combined on the cone fixing bar 8 by using a nut 7. Then, in order to adjust the focusing position of the ultrasonic wave to the position of the tumor by using the external control device 20, a command signal is sent to the moving means 19 of the focused ultrasonic wave generator 1, and then it is moved. When the focusing position coincides with the tumor, a command signal is sent to the oscillator 14 through the CPU 17, by using the external control device 20. An ultrasonic wave is generated from the ultrasonic wave generator 4 by using a signal which is amplified by the amplifier 15.

In this way, a generated ultrasonic wave is reflected from a reflecting surface of the conical reflector having a different top angle, toward a different direction by the combination of cone reflecting surfaces. As a result, the reflected ultrasonic wave comes to the rotating, paraboloidal, reflecting surface 3 of the paraboloidal, reflecting case 2, having a different angle. Generally, considering the characteristic of a paraboloid, an ultrasonic wave entering in parallel with the central axis of the paraboloid, is focused on its focus, but, an ultrasonic wave having a certain receiving angle, has a different focusing position depending on the receiving angle.

Therefore, when an ultrasonic wave is reflected by the conical reflecting surface in a different direction and received by the rotating, paraboloidal surface, is it focused on a different position depending on each receiving angle. As a result, the focusing condition of ultrasonic waves will be obtained depending on the combination of conical reflecting surfaces. That is, a therapeutic ultrasonic wave can be focused suitably depending on the condition of a tumor or a calculus in the body of a patient, only by the selection and combination of the conical reflecting surfaces.

In this manner, a surgeon confirms the condition of a position to be treated by using an ultrasonic wave observing probe before medical treatment, and selects an adequate combination of conical reflectors having different top angles depending on the condition, and therefore an ultrasonic wave can be focused most effectively for medical treatment. The focused condition of ultrasonic waves can be changed freely and simply so as to allow fast and suitable treatment.

Figure 2:
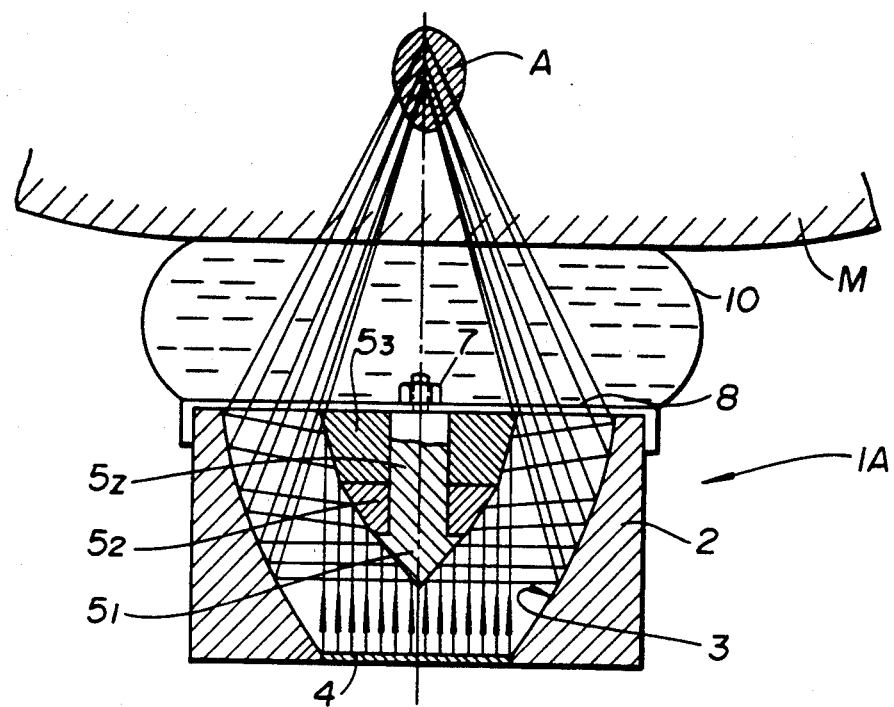
FIG. 2 is a cross sectional view of a converged ultrasonic wave generator in the ultrasonic wave therapeutic device according to the second embodiment of the present invention.

FIG. 2 is a cross sectional view of a focused ultrasonic wave generator 1A in an ultrasonic wave therapeutic device according to the second embodiment of the present invention. The general construction of this ultrasonic wave therapeutic device is the same as that of the previously described, first embodiment. Therefore only different points of the essential parts will be described. When a tumor in the human body M is large, therapeutic ultrasonic waves can be focused in a wide area. Therefore, in the second embodiment, three kinds of conical reflectors having a different top angle, are accumulated. That is, seeing from the ultrasonic wave generator 4, the first conical reflector $5_1$, the second conical reflector $5_2$ and the third conical reflector $5_3$ are fixed, in this order, to a supporting axis $5_z$ by using a nut 7.

In this way, ultrasonic waves generated from the ultrasonic wave generator 4, are reflected in a plurality of directions, by using three kinds of conical reflecting surfaces, and received by the reflecting surface 3 of the paraboloidal, reflecting case 2 having so many receiving angles, and therefore the ultrasonic waves can be focused on the wider area.

In this manner, the focusing condition of ultrasonic waves can be changed only by changing the combination of the conical reflecting surfaces.

Figure 3:
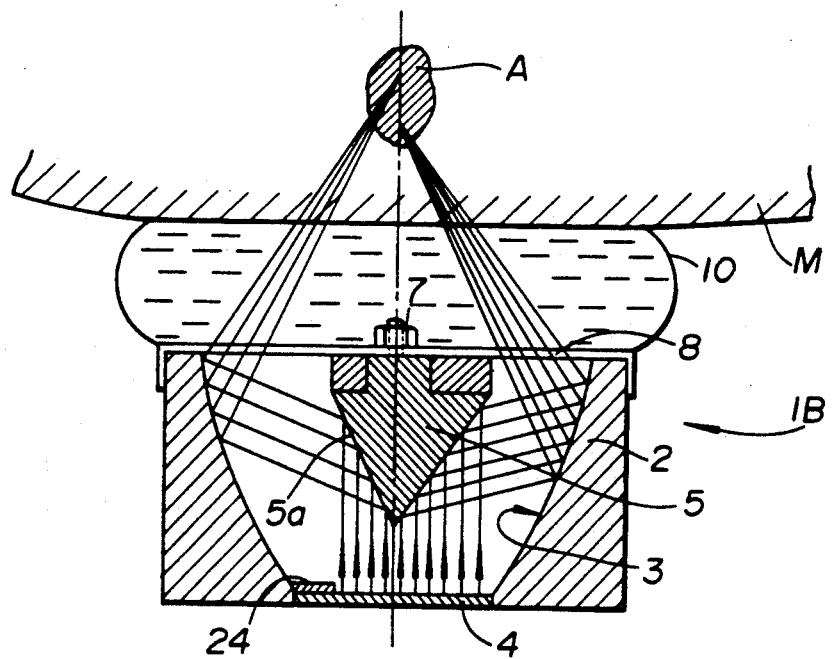
FIG. 3 and FIG. 4 are cross sectional views of converged ultrasonic wave generators, respectively, in the ultrasonic wave therapeutic device according to the third and fourth embodiments of the present invention.

FIG. 3 is a cross sectional view of a focused ultrasonic wave generator 1B of the ultrasonic wave therapeutic device according to the third embodiment of the present invention. The general construction of this ultrasonic wave therapeutic device is the same as that of the first embodiment, so the same components are not explained and, only the difference of the essential parts will be described.

In this embodiment, right and left reflecting surfaces of the conical reflector 5 are different as shown in FIG. 3, having a different top angle. Therefore, combination of the top angles of conical reflecting surfaces is different from that of the above described first and second embodiments. That is, it is possible to combinate the top angles of the cone as shown in the third embodiment, and, its fundamental functions and effects are the same as those of the first embodiment.

In this third embodiment, an ultrasonic wave control member 24 is placed on a suitable position of the ultrasonic wave generator 4 so as to cut ultrasonic wave components which cannot be reflected to the paraboloidal reflecting surface 3 after they are received by a reflecting surface $5_a$ of the conical reflector 5.

Figure 4:
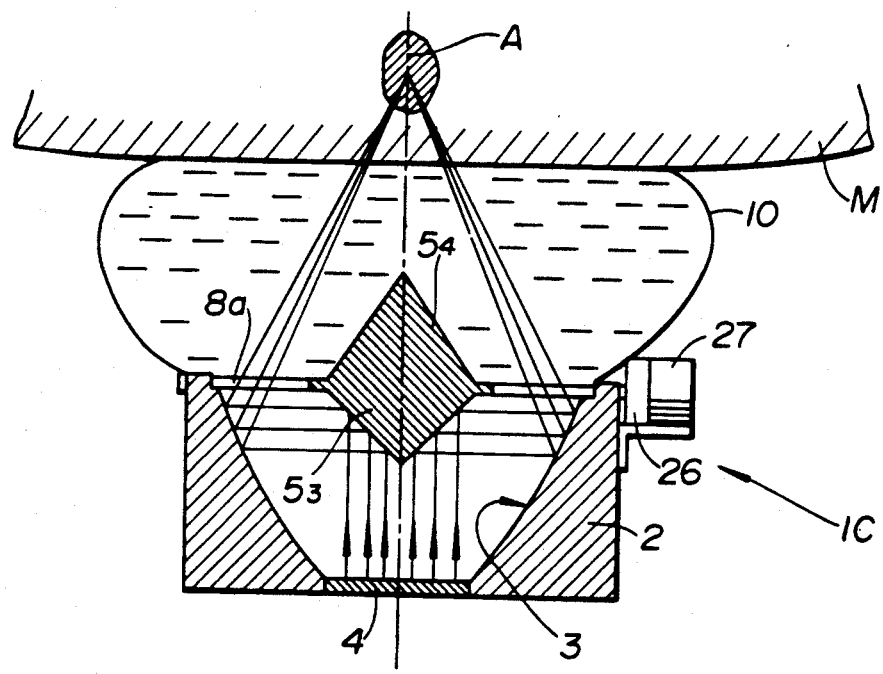

FIG. 4 is a cross sectional view of a focused ultrasonic wave generator 1C of the ultrasonic wave therapeutic device according to the fourth embodiment of the present invention, and, the general construction of the ultrasonic wave therapeutic device of this embodiment is the same as that of the above described, first embodiment.

In order to change the receiving angle of an ultrasonic wave which is received by the rotating, paraboloidal reflecting surface 3, the first conical reflecting body $5_3$ and the second conical reflecting body $5_4$ are formed as one body, facing their top angles in opposite directions, and, the lower part of each reflecting body is fixed to a cone fixing bar $8_a$. The cone fixing bar $8_a$ is fixed rotatably to the reflecting case 3, and rotated by a stepping motor 27 through a decelerator.

According to the fourth embodiment of the above described construction, a surgeon looks at the condition of a tumor and sends a signal to the stepping motor 27, rotating the cone fixing bar 8a with a predetermined angle, and selecting either one of the conical reflectors 5₃ and 5₄, and then a desired focusing condition of an ultrasonic wave is obtained to do the most suitable medical treatment.

In the first to fourth embodiments that are mentioned above, a suitable focusing condition of therapeutic ultrasonic waves can be obtained only by selecting the combination of conical reflectors which have a different top angle, depending on the condition of a position of a patient to be treated, so that reliable medical treatment can be done by using a simple construction and procedure.

Figure 5:
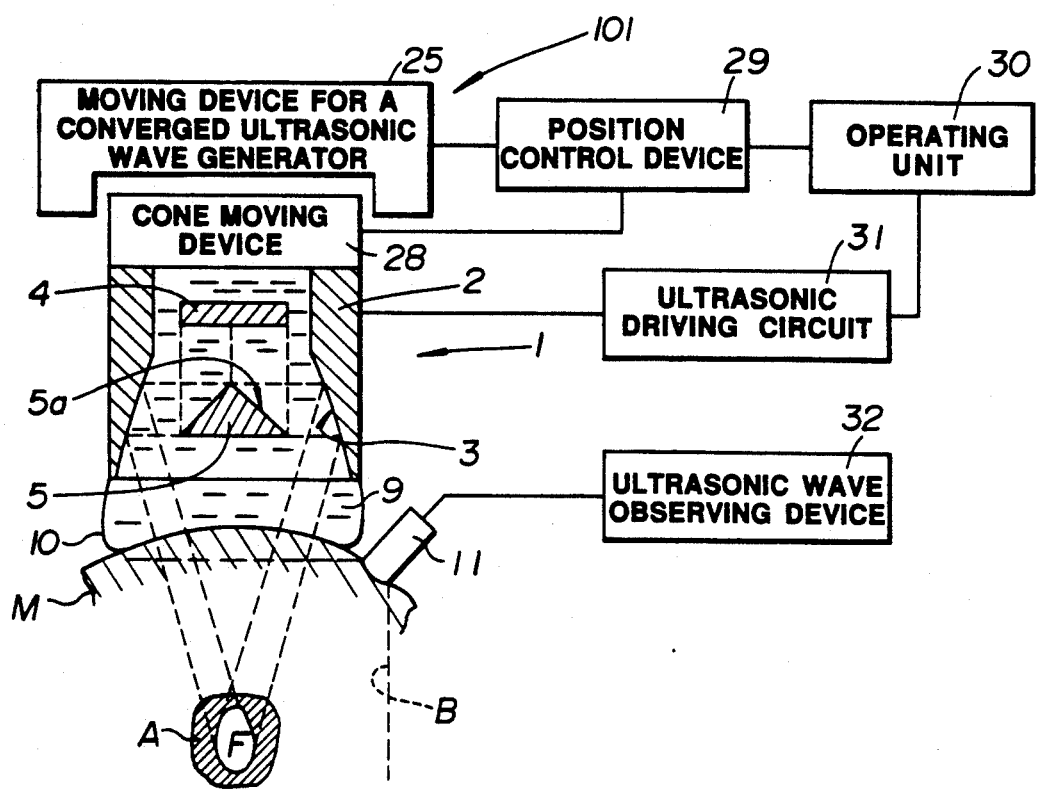
FIG. 5 is a schematic constructional diagram of the fifth embodiment of an ultrasonic wave therapeutic device according to the present invention.

FIG. 5 is a schematic constructional diagram of the whole of an ultrasonic wave therapeutic device 101 according to the fifth embodiment of the present invention. An ultrasonic wave oscillator 1 used for medical treatment, is made of copper or brass; and, its main part is constructed with a reflecting case 2 having a paraboloidal, inner reflecting surface, an ultrasonic wave oscillator 4 of piezoelectric elements of PZT or a Langeban oscillator which is arranged on the upper part of the reflecting case 2, and a conical reflector 5, made of copper or brass having a conical reflecting surface 5ₐ, which is facing to an ultrasonic wave irradiating surface of the ultrasonic wave oscillator. The conical reflector 5 is arranged in the reflecting case 2, in such a way that it faces the reflecting surface 3 of the reflecting case 2. Moreover, the conical reflector 5 can be moved freely, corresponding to the reflecting surface 3 in the reflecting case 2.

On the lower part of the above described, reflecting case 2, a water bag 10 made of soft resin etc. is provided as one body with the reflecting case 2; and, an ultrasonic wave transmitting liquid 9, for example air-removed water is filled in the water bag 10 and the reflecting case 2. The conical reflector 5 can be moved by using a cone moving device 28, which is mounted on the reflecting case 2 and connected with an operating unit 30 through a position control device 29. The ultrasonic wave oscillator 4 is also connected with the operating unit 30 through an ultrasonic wave driving circuit 31. The operating unit 30 is connected with a moving device 25 of the focused ultrasonic wave oscillator through the position control device 29.

An ultrasonic wave probe 11 is fixed on the lower side of the ultrasonic wave oscillator 1, by using a mechanism not shown, so as to observe an image of a tumor A to be treated in the human body M; and, a signal detected by the probe 11 is displayed as an image to be observed, by using an ultrasonic wave observing device 32.

Figure 6:
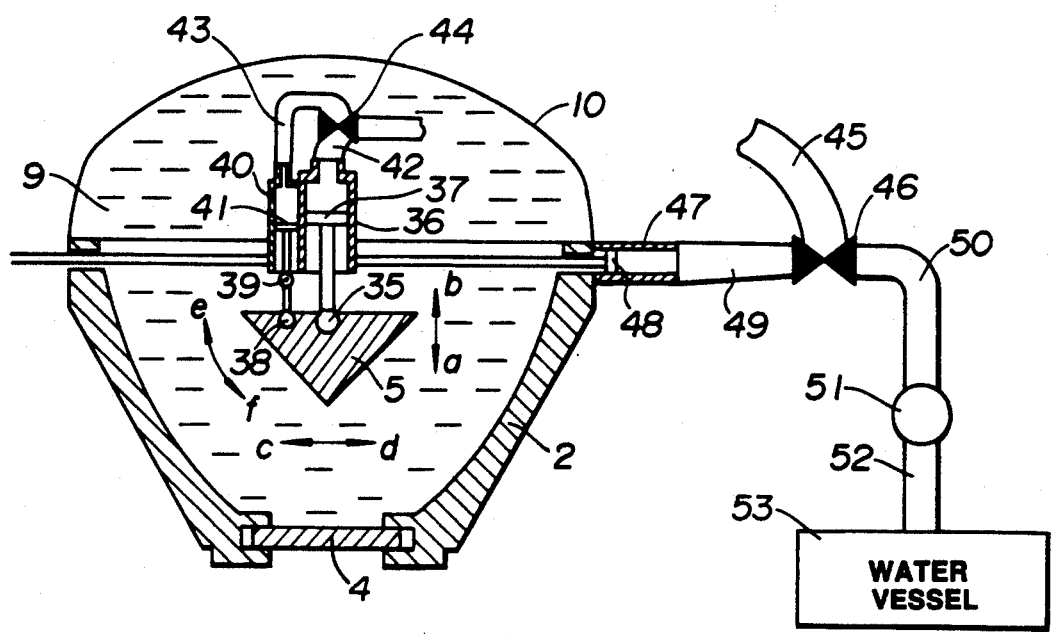
FIG. 6 is an enlarged cross sectional view of an essential part of a cone moving device illustrating its concrete construction in the fifth embodiment of the ultrasonic wave curing device according to the present invention.

FIG. 6 shows an example of moving mechanism of the conical reflector 5 in the above described, cone moving device 28.

In the conical reflector 5 having a conical reflecting surface, a center position of the bottom surface is connected with a first piston 37, which is moved by a first ball joint 35 in a first cylinder 36. In the vicinity of the ball joint 35, a second ball joint 38 is arranged, and its ball side is fixed to the conical reflector 5, and, the other end of the ball joint 38 is coupled with a second piston 41 which moves in a second cylinder 40, through a joint 39. The first cylinder 36 and the second cylinder 40 are connected with a first switching valve 44 by using, respectively, a first hose 42 and a second hose 43. The first switching valve 44 is is connected with a second switching valve 46 through a third hose 45. Each side of the first cylinder 36 and the second cylinder 40 is connected with a third piston 48, which moves in a third cylinder 47. The third cylinder 47 is connected with the second switching valve 46 through a fourth hose 49, the second switching valve 46 is connected with a pump 51 through a fifth hose 50, and, the pump 51 through a fifth hose 50, and, the pump 51 is connected with a water vessel 53 through a sixth hose 52.

In the ultrasonic wave therapeutic device 10 of the fifth embodiment which has the above described construction, the focused ultrasonic wave oscillator 1 is contacted with a surface of the human body M through the water bag 10 as shown in FIG. 5. An ultrasonic probe 11 is adhered to the position of a tumor A of the human body M so as to obtain an image signal in a observing area B by using the probe 11, and, a tomogram is obtained by using an ultrasonic wave observing device 32.

A surgeon looks at the tomogram, and operates the operating unit 30 to send a command to the position control device 29, depending on the position and size of the tumor A. In this way, the conical reflector 5 is moved by using the cone moving device 28, and the focusing area F of the ultrasonic waves is made to coincide with the position of the tumor A. The surgeon operates the operating unit 30, sends a command to the ultrasonic wave driving circuit 31 to drive the ultrasonic wave oscillator 4, and an ultrasonic wave is generated. Then, the ultrasonic wave generated is reflected by the conical reflecting surface 5ₐ of the conical reflector 5, and reflected, again, by the inner reflecting surface 3 of the reflecting case 2 so as to be focused on a focusing area F, and therefore the tumor A is treated medically.

In the next place, we will describe a reflector moving means which adjusts the focusing position by moving the conical reflector 5, referring to FIG. 6. At first, when the conical reflector (called a cone, hereafter) 5 is forced to move toward the arrow b, a surgeon operates the operating unit 30, and opens the first switching valve 44 in such a way that the first hose 42 and the second hose 43 pass through the third hose 45, and then opens the second switching valve 46 in such a way that the third hose 45 is in fluid communication with the fifth hose 50 so as to drive the pump 51. The pump 51 sucks in water from the first cylinder 36 and the second cylinder 40, moving the first piston 37 and the second piston 41 toward the arrow b, which leads the cone 5 to move toward the arrow B. When the cone 5 is forced to move toward the arrow a, the pump 51 is made to rotate reversely so as to supply water from a water vessel 53 to the first cylinder 26 and the second cylinder 40, so that the first piston 27 and the second piston 41 are pushed down to move the cone 5 toward the arrow a.

In the next place, when the cone 5 is made to move toward an arrow c, a surgeon operates the operating unit 30 to switch the second switching valve 46, in such a way that the fourth hose 49 is in fluid communication with the fifth hose 50, to drive the pump 51, to supply water from the water vessel 53 to the third cylinder 47, and to move the third piston 48 toward the arrow c. In this way, both of the cone 5 and the third piston 48 move toward the arrow c. On the other hand, when the cone 5 is made to move toward an arrow d, the pump 51 is rotated reversely in the above described condition of valves, so as to suck in water from the third cylinder 47 and pull the third piston 48, and, the cone 5 moves toward the arrow d.

Moreover, in order to rotate the cone 5 toward the arrow e, a surgeon operates the operating unit 30 to open the first switching valve 44, in such a way that the second hose 43 and the third hose 45 are in fluid communication. The surgeon switches the second switching valve 46 so that the third hose 45 and the fifth hose 50 are in fluid communication. After that the surgeon drives the pump 51 to suck in water from the second cylinder 40, so the second piston 41 is pulled toward the arrow, and the cone 5 is pulled toward the arrow e through the joint 39. Thus, the cone 5 rotates toward the arrow 'e' on the center of the ball of the first ball joint 35. If it is intended to rotate the cone 5 toward an arrow f, the pump 51 is made to rotate reversely in the above described valve condition so as to supply water from the water vessel 53 to the second cylinder 40, and the second piston 41 is pushed down, and therefore the cone 5 rotates toward the arrow f.

Figure 7:
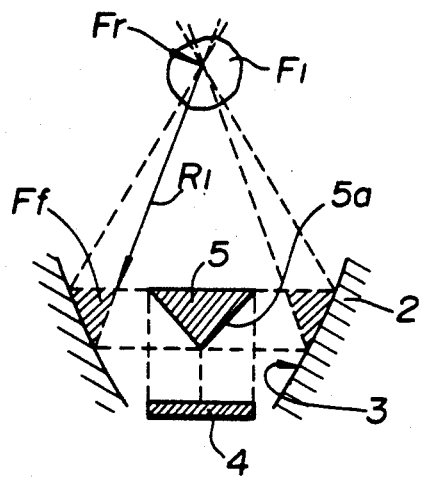
FIG. 7 (A) and (B)
Figure 7:
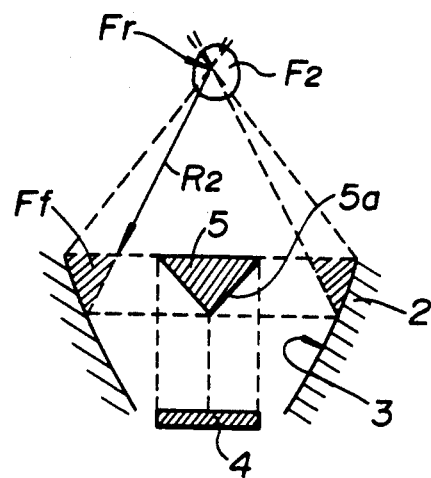
Figure 8:
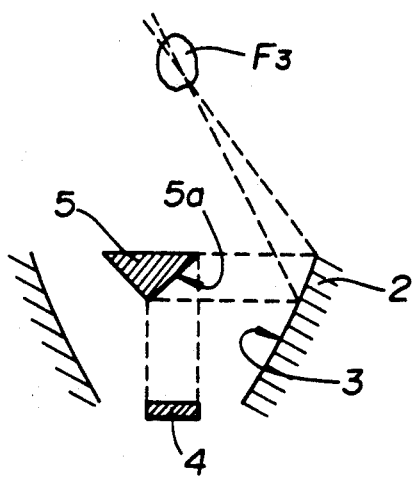
FIG. 8 and FIG. 9 illustrate operation of the cone moving device of FIG. 6.
Figure 9:
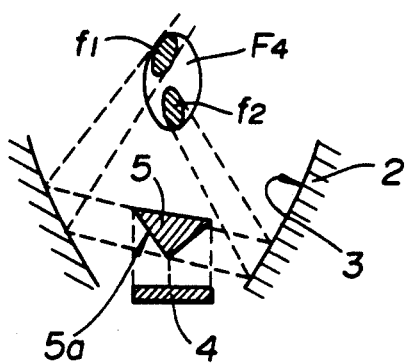

FIG. 7 to FIG. 9 illustrate, respectively, the focusing condition of ultrasonic waves, when the cone 5 is moved to various positions by using the above described moving means for a reflector.

FIG. 7 (A) shows the focusing condition of an ultrasonic wave, when the cone 5 is moved toward the arrow a in FIG. 3, and FIG. 7 (B) shows the focused condition of an ultrasonic wave, when the cone 5 is moved toward the arrow b. Comparing both of the focusing conditions with each other, in this case, a geometrical focus of the parabolic, inner reflecting surface 3 of the reflecting case 2 is Fr in FIG. 7 (A) and (B), a crossing area of an ultrasonic wave which is reflected by the paraboloidal, inner reflecting surface 3 of the reflecting case 2, and an ultrasonic wave which is reflected by the conical reflecting surface $5_a$ of the cone 5, is Ff. The distances of the crossing area Ff and the geometrical focus Fr of the paraboloid are, respectively, $R_1$ and $R_2$, and the relationship $R_1 > R_2$ remains as is clear from FIG. 7 (A) and (B).

As ultrasonic waves are focused on the focusing area F, it is considered equivalently that the ultrasonic wave is irradiated from ultrasonic wave oscillators which have the shape of a circular shell having curvature radii of $R_1$ and $R_2$, respectively. Therefore, as an ultrasonic wave is focused sharply when the curvature radius of the ultrasonic wave oscillator of circular shell type is small, it is considered that a focusing area $F_2$ (refer to FIG. 7 (B)), in which the cone 5 is near the geometrical focus Fr of the paraboloid, is focused more sharply than a focusing area $F_1$ (Refer to FIG. 7 (A)), in which the cone 5 is far from the focus Fr.

In the next place, FIG. 8 shows a focusing condition when the cone 5 moves toward the arrow c (Refer to FIG. 6). An ultrasonic wave generated from the ultrasonic wave oscillator 4, is reflected only by the right half of the conical reflecting surface $5_a$ of the cone 5. The reflected ultrasonic wave goes toward only the right half of the inner reflecting surface 3 of the reflecting case 2, and is reflected, again, by the right half of the inner reflecting surface 3, and then is focused on the focusing area $F_3$.

FIG. 9 shows a focusing condition, when the cone 5 turns toward the arrow e (Refer to FIG. 6) and is inclined. An ultrasonic wave generated from the above described ultrasonic wave oscillator 4, is reflected by the conical reflecting surface $5_a$ of the cone 5, but, as the cone 5 has inclined, an ultrasonic wave reflected by the cone 5, is irradiated with a different receiving angle, to the inner reflecting surface 3 of the reflecting case 2, because the receiving angle is equal to the reflecting angle in ultrasonic waves. In this way, as each ultrasonic wave reflected from the inner reflecting surface 3 has a different reflecting angle, the ultrasonic waves reflected from the inner reflecting surface 3 are focused on the areas $f_1$ and $f_2$, as shown in the cross sectional view of FIG. 9. Actually, the ultrasonic waves are reflected from the reflecting case 2 with a series of different reflecting angles, so the focusing area of ultrasonic wave waves becomes so wide as $F_4$.

In this manner, an ultrasonic wave therapeutic device 101 according to the fifth embodiment, has the following effects depending on the moving direction of the cone 5.

That is, as shown in FIG. 7 (A) and (B), the cone 5 moves in parallel with the central axis of the ultrasonic oscillator 4, so the width of focusing ultrasonic waves changes at the position of focus Fr, and therefore tumors having a various kind of therefore tumors having a various kind of sizes and widths can be treated effectively. And, when the cone 5 moves perpendicular to the central axis of the ultrasonic wave oscillator 4 as shown in FIG. 8, a transmitting path of an ultrasonic wave changes greatly. Thus, if an ultrasonic wave is prevented from irradiating a tumor etc. by an obstacle, for example a bone, it is possible to avoid the obstacle and irradiate the ultrasonic wave to the tumor for medical treatment. And, as shown in FIG. 9, if the cone is inclined, a heating area of ultrasonic waves extends toward the central axis of the ultrasonic wave oscillator 4, and a long heating area is formed, and therefore a large tumor can be treated effectively by inclining the cone 5.

Figure 10:
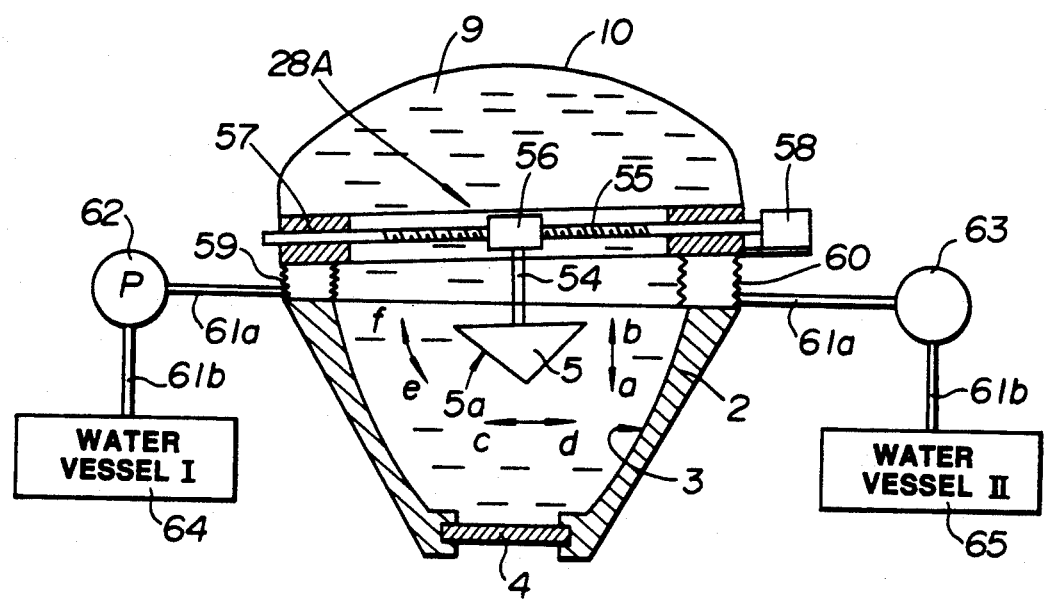
FIG. 10 is an enlarged cross sectional view of an essential part of the cone moving device illustrating its concrete construction in the sixth embodiment according to the present invention.

FIG. 10 is a cross sectional view of an essential part of an ultrasonic wave therapeutic device according to the sixth embodiment of the present invention. The ultrasonic wave therapeutic device according to the sixth embodiment is constructed in the same way as the ultrasonic wave therapeutic device 101 of the above described first embodiment except for the cone moving device 28, so the same components are shown by the same symbols, omitting their detailed description.

Figure 11:
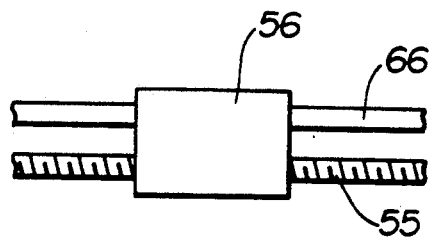
FIG. 11 is a plan view of a slider in the above illustrated FIG. 10.

A cone moving means 28A of the sixth embodiment is connected with a slider 56, which moves the central position of the bottom surface of the cone 5 by using a supporting shaft 54 and a ball screw 55. Both of the ends of the ball screw 55 are rotatably coupled to a ring 57 of a bearing; and, one end is connected to the output shaft of a motor 58. And, the above described ring 57 is mounted on the open end of the focusing side of the reflecting case 2, by using first and second bellows 59, 60. The first bellows 59 and the second bellows 60 are, respectively, connected with a first pump 62 and a second pump 63, through a hose 61a, and, the first pump 62 and the second pump 63 are, respectively, connected with a first water vessel 64 and a second water vessel 65, through a hose 61b. FIG. 11 is an enlarged plan view of an essential part of the slider 56, seeing from the side of the water bag 10. The slider 56 is passed through a slider-guide shaft 66, as well as through the ball screw 55.

In the above constructed ultrasonic wave curing device according to the sixth embodiment, the cone moving device 28A has the following functions. When the cone 5 is made too move toward the arrow c or d, the motor 58 is rotated in the forward or the backward direction, so, the ball screw 55 is rotated to progress the slider 56 along the slider-guide shaft 66 in the direction of the arrow c or the arrow d, and therefore the cone 5 is moved.

When the cone 5 is intended to move toward the arrow a, the first pump 62 and the second pump 63 are driven to suck in the same volume of water from the first bellows 59 and the second bellows 60, and both the first bellows 59 and the second bellows 60 are folded and compressed so as to move the cone 5 and the ring 57 toward the arrow b. On the other hand, if the cone 5 is intended to move toward the arrow b, the first pump 62 and the second pump 63 are rotated in the reverse direction, and the same volume of water is supplied from the first water vessel 64 to the first bellows 59, and from the second water vessel 65 to the second bellows 60, and then both of the bellows 59 and 60 are at first expanded, and after that compressed, and therefore the cone 5 is moved toward the arrow b.

Moreover, when the cone 5 is moved toward the arrow e and inclined, the first pump 42 is driven so as to suck in water from the first bellows 59, or the second pump 63 is driven so as to flow water in the second bellows 60, and then the ring 57 is moved with the cone 5 toward the arrow e. On the other hand, when the cone 5 is turned toward an arrow f so as to be inclined, the first bellows 59 and the second bellows 60 suck in, or supply water in the reverse direction against when the cone 5 is inclined toward the arrow e, and then the ring 57 is inclined toward the arrow f together with the cone 5.

This second embodiment has the same effect as the above described first embodiment, and, as only a small part projects to the bottom surface of the cone, the water bag 10 can be adhered to the human body more easily, and the heating position can easily coincide with the position of a tumor.

Figure 12:
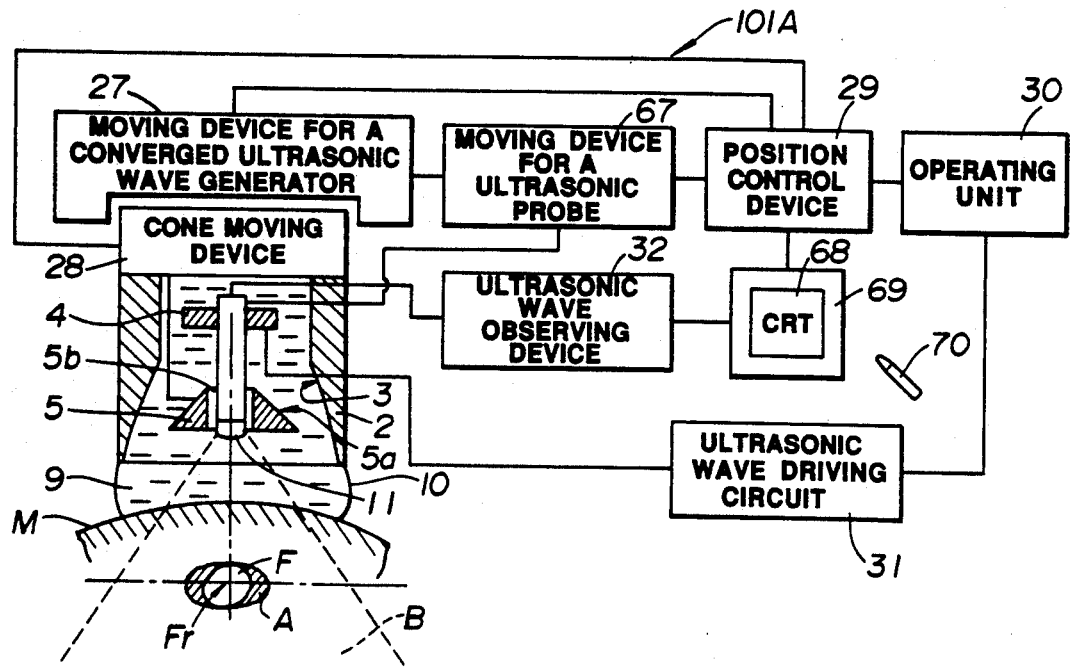
FIG. 12 is a schematic constructional view of an ultrasonic wave therapeutic device modified from the ultrasonic wave therapeutic device shown in FIG. 5.

FIG. 12 is a schematic constructional diagram of the whole of an ultrasonic curing device 101A, illustrating the first modification of the device shown in FIG. 5. As the modified ultrasonic wave therapeutic device 101A has the same construction as the ultrasonic wave therapeutic device 101 of the previously described first embodiment except for the ultrasonic wave observing means, the same components has the same symbols, and only the different points will be described.

In this modified ultrasonic wave therapeutic device 101A, the ultrasonic wave probe 11 is arranged on the axis which runs through the geometrical focus Fr of the paraboloidal, inner reflecting surface of the reflecting case 2. The ultrasonic wave probe 11 is mounted on the reflecting case 2 in such a way that the central axis of the probe coincides with that of the ultrasonic wave oscillator 4. The ultrasonic wave probe 11 is connected with an ultrasonic wave probe moving device 67, which is connected with the position control device 29.

The cone 5 having the conical reflecting surface 5a, is provided with a hole 5b on its central axis, and, the ultrasonic wave probe 11 is being inserted into the hole 5b. The probe 11 is connected with an image displaying device 68 comprising CRT, through the ultrasonic wave observing device 32, and, on the front surface of the displaying device 68 is fixed a touch panel 69. An indicating pen 70 is provided for giving instructions to the touch panel 69. The touch panel 69 is connected with the position control device 29 in order to send information which is indicated by the indicating pen 70 to the position control device 29.

The ultrasonic wave therapeutic device 101A of the above described construction according to the modified embodiment, has the same function as the fifth embodiment, but the control means for the focusing area F is different.

That is, a surgeon operates the operating unit 30 to sent a command to the position control device 29, and, by using the ultrasonic wave moving device 67, the ultrasonic wave probe 1 is inclined, or moved upward and downward. Then, a tomogram of an observing area B in the human body M, is displayed on the image displaying device 68 through the ultrasonic wave observing device 32.

Here, a surgeon indicates the position of the outline of a tumor on the touch panel 69, by using the indicating pen 70. Then, the information is sent to the position control device 29, which sends a command to the cone moving device 28, and moves the cone 5 depending on the information, namely the size of the tumor A. In the next place, the surgeon operates the operating unit 30, and drives the ultrasonic wave oscillator 4 through the ultrasonic wave driving circuit 31 for the medical treatment.

Such a modified embodiment of the ultrasonic wave therapeutic device 101A, has the same effect as that of the previously described, fifth embodiment, and, as the ultrasonic wave probe 11 is in the reflecting case 2, the device can be made smaller. Moreover, the focusing area F of ultrasonic waves is always in the observing area B, so it is easy to position the device. As the heating area can be controlled simply and certainly depending on the size of a tumor, the efficiency of treatment can be increased.

Figure 13:
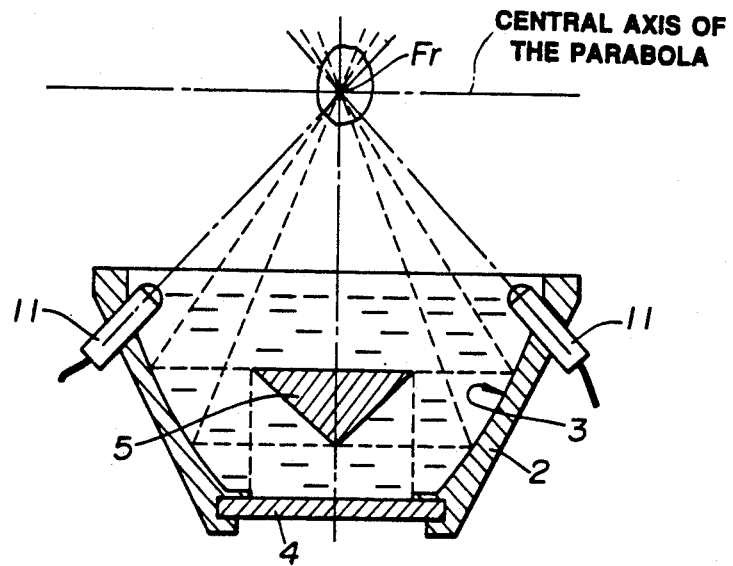
FIG. 13 is an enlarged cross sectional view of an essential part of an ultrasonic wave generator in another modified embodiment of the ultrasonic therapeutic device shown in FIG. 5.

In the next place, FIG. 13 is a schematic constructional view of an essential part of another modification of the ultrasonic wave therapeutic device shown in FIG. 5. In the ultrasonic wave therapeutic device according to this embodiment, two or more ultrasonic wave probes 11 are mounted on the inner peripheral reflecting surface of the reflecting case 2, on the axis which runs through the geometrical focus Fr of the paraboloidal reflecting surface 3 of the reflecting case 2. The other construction is the same as that of the above described FIG. 10.

The ultrasonic wave therapeutic device of the modified embodiment having the above described construction, functions fundamentally in the same way as the previously described, modified embodiment, and has the same effects. At least two ultrasonic wave probes are provided. Thus, if an obstacle, for example a bone, is in the transmitting path of an ultrasonic wave coming form one ultrasonic wave probe, another probe can be used for observing a position to be treated.

Figure 14A:
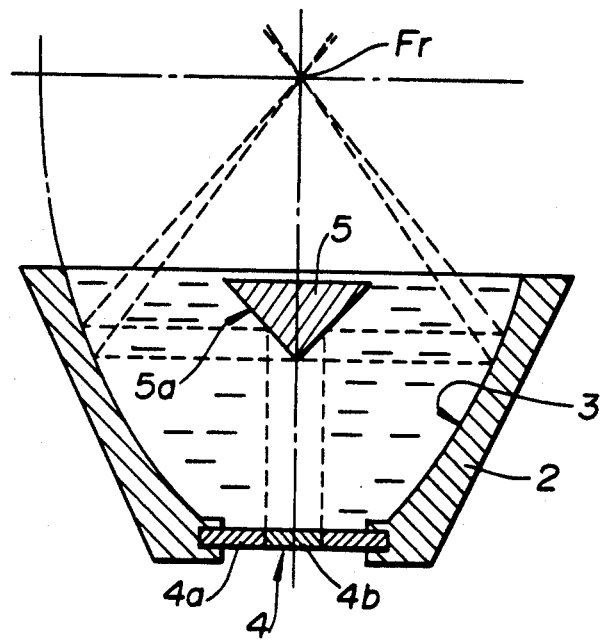
FIG. 14 (A) and (B) are enlarged cross sectional views of essential parts of ultrasonic wave generators modified in another way from the ultrasonic wave generator shown in FIG. 5, in this case, FIG. 14 (A) is an operational diagram of an ultrasonic wave oscillator used for observation, and, FIG. 14 (B) is an operational diagram of an ultrasonic wave oscillator for treating objects.
Figure 14B:
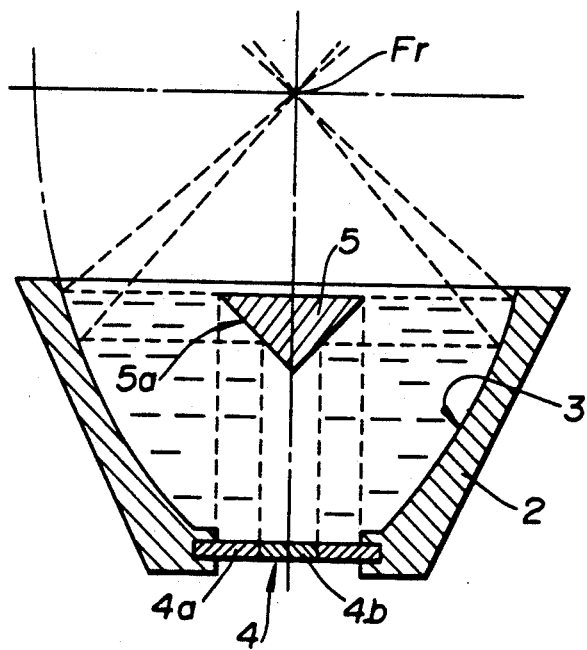

FIG. 14 (A) and (B) are schematic constructional views of essential parts of other modified examples of the ultrasonic wave therapeutic device shown in FIG. 5. FIG. 14 (A) illustrates an observing condition by using ultrasonic waves, and FIG. 14 (B) illustrates a treatment condition by using ultrasonic waves. In such a modified ultrasonic wave therapeutic device, the ultrasonic wave oscillator 4 is constructed with an ultrasonic wave oscillator 4a for treatment, and an ultrasonic wave oscillator 4b for observing; and, they are mounted on the reflecting case 2, in such a way that the central axis of the ultrasonic wave oscillator 4a for treatment, coincides with the central axis of the ultrasonic wave oscillator 4b having a higher frequency for observation. Its other construction is the same as that of the previously described fifth embodiment.

In the ultrasonic wave therapeutic device of this embodiment having the above described construction, and ultrasonic wave of higher frequency which is generated form the ultrasonic wave oscillator 4b for observing, is reflected by the conical reflecting surface 5a of the cone 5, and, reflected again, by the paraboloidal inner reflecting surface 3 of the reflecting case 2 so as to be focused on the part of a tumor. This transmitting path of the ultrasonic wave is the same as that of the ultrasonic wave oscillator 4a for treatment.

As a tumor has a different acoustic impedance form that of normal living tissue, an ultrasonic wave for treatment is reflected. And, the reflected ultrasonic wave is transmitted toward the reverse direction, and returns to the observing, ultrasonic wave oscillator 4b, and therefore the reflected wave gives information of the position of the tumor. The other functions are the same as that of the previously described fifth embodiment.

Thus, in the ultrasonic wave therapeutic device according to this modified embodiment, the focusing area F of the ultrasonic wave oscillator 4a for treatment, coincides with that of the ultrasonic wave oscillator 4b for observing, and therefore correct information of a treatment position can always be obtained.

In the above described fifth and sixth embodiment, the cone having a conical reflecting surface can be moved in the ultrasonic wave oscillator by using a simple construction, so the heating area can be changed smoothly, and continuous medical treatment can be given without interruption.

FIG. 15 is a schematic constructional diagram of the whole of the ultrasonic wave therapeutic device 101 according to the seventh embodiment of the present invention. The main part of the focused ultrasonic wave oscillator 1 for treatment, is constructed with a reflecting case 2 made of copper or brass, and having the reflecting surface 3, which is formed as a paraboloidal, inner reflecting surface with a plurality of focuses; an ultrasonic wave oscillator 4 comprising a piezoelectric element of PZT or the Langeban oscillator; and a conical reflector 5 made of copper or brass, and having a conical reflecting surface 5a opposite to the ultrasonic wave irradiating surface of the ultrasonic wave oscillator 4, and being arranged in the reflecting case 2, in such a way that the reflector 5 is facing to the reflecting surface 3 in the reflecting case 2. As will be described later, the conical reflector 5 can be moved freely corresponding to the reflecting surface 3 in the above described reflecting case 2.

In the lower part of the reflecting case 2, is provided a water bag 10 of soft resin etc. as one body with the reflecting case 2. In the water bag 10 and the reflecting case 2 is filled an ultrasonic wave propagating fluid, for example air-removed water. The conical reflector 5 can be moved by using a cone moving device 28, which is arranged in the reflecting case 2, and connected with an operating unit 30 through a position control device 29. The ultrasonic wave oscillator 4 is also connected with the operating unit 30 through an ultrasonic wave driving circuit 31, and, the operating unit 30 is connected with the moving device of the focused ultrasonic wave oscillator 27 through the position control device 29.

The ultrasonic wave probe 11 is mounted on the lower side of the ultrasonic wave oscillator 1 by a mechanism not shown in the figure, so as to be able to observe an image of the tumor A to be treated in the human body M. In this case, an observing signal detected by the probe 11 is displayed, as an observing image by using an ultrasonic wave observing device 32.

Figure 16:
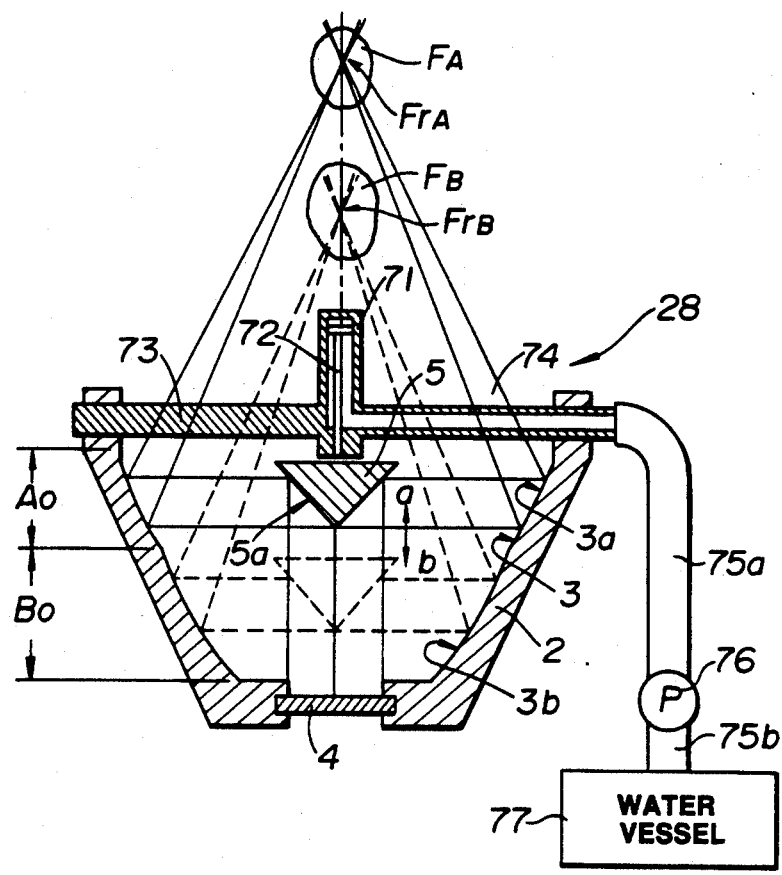
FIG. 16 is an enlarged cross sectional view of an essential part of the cone moving device illustrating its concrete construction and the shape of the inner reflecting surface of the ultrasonic wave therapeutic device according to the seventh embodiment of the present invention.

FIG. 16 shows an example of the moving mechanism of the conical reflector 5 in the above described cone moving device 28. The central position of the bottom surface of the conical reflector 5 having a conical reflecting surface, is fixed to a piston 72 which moves upward and downward in a cylinder 71, and arranged in the reflecting case 2; one end surface of the cylinder 71 is coupled to a support member 73 of bar type, and the other end surface is coupled to a pipe 74 which passes through the cylinder, so, the cylinder 71 is fixed to a portion near the open end of the reflecting case 2. The pipe 74 passing through the cylinder 71, is connected with a pump 76 through a hose 75a, and the pump 76 is connected with a water vessel 77 through a hose 75b.

The paraboloidal, inner reflecting surface 3 in the reflecting case 2 is so constructed that a paraboloidal, inner reflecting surface 3a of the upper section $A_o$ includes a geometrical focus $F_{rA}$, and that a paraboloidal, inner reflecting surface 3b of the lower section $B_o$ includes a geometrical focus $F_{rB}$.

In the ultrasonic wave therapeutic device 101 of the seventh embodiment having the above described construction, at first the ultrasonic wave oscillator 1 is so placed that the water bag 10 is contacted with the surface of the human body M, as is shown in FIG. 15, and then the ultrasonic wave probe 11 is adhered to the surface of the human body, pointing at the tumor A to be treated. In this manner, an image signal of the observing area B is detected by using the ultrasonic wave probe 11, and a tomogram is formed by using the ultrasonic wave observing device 32.

Looking at the tomogram, a surgeon operates the operating unit 30 depending on the position or size of the tumor A, sends a command to the position control device 29 so as to operate the cone moving device 28 and to move the conical reflector 5, and therefore the focusing area F of ultrasonic waves coincides with the position of the tumor A. The surgeon then operates the operating unit 30 to send a command to the ultrasonic wave driving circuit 31, to drive the ultrasonic wave oscillator 4, and to generate ultrasonic waves. An ultrasonic wave generated from the ultrasonic wave oscillator 4 is reflected by the conical reflecting surface 5a of the conical reflector 5 which is arranged opposite to the oscillator 4, approximately in the horizontal direction, toward the inner peripheral reflecting surface 3 of the reflecting case 2. By the inner peripheral reflecting surface 3, the wave is reflected, again, toward a portion to be treated and focused on the focusing area F. Therefore, by using the focused ultrasonic waves, the tumor A is warmed and treated.

Now, referring to FIG. 16, we will describe how to change the position of the focused area F, when the conical reflector 5 is moved by the cone moving device 28.

At first, when the conical reflector 5 is made to move toward the arrow 'a', a surgeon operates the operating unit 30 so as to drive the pump 76, and to supply water from the water vessel 77 into the cylinder 71. And, as the piston 72 is lifted up, the reflector 5 moves toward the arrow a. Here, the ultrasonic wave oscillator 4 is driven, so an ultrasonic wave is reflected by the conical reflecting surface 5a of the reflector 5 the reflected wave is one more reflected by the paraboloidal, inner reflecting surface 3a so as to be focused on the focusing area $F_A$.

When the reflector is made to move toward the arrow b, the pump 76 is rotated in the reverse direction, and sucks in water from the cylinder 71 to push down the piston 72 toward the arrow b. Therefore, the reflector 5 is moved toward the arrow b. Here, the ultrasonic wave oscillator 4 is driven, so an ultrasonic wave is reflected by the conical reflecting surface 5a, and the reflected ultrasonic wave is once more reflected by the inner peripheral reflecting surface 3b so as to be focused on the focusing area $F_B$.

According to the ultrasonic wave therapeutic device of the seventh embodiment, a surgeon can change the focusing position of ultrasonic waves only by moving the conical reflector 5 to the central axis of the ultrasonic wave oscillator 4, so two or more position scan be treated, and therefore effective treatment can be made with simple operation.

And, in the above described seventh embodiment, it is needless to say that the paraboloidal, inner reflecting surface can have two or more focuses.

Figure 17:
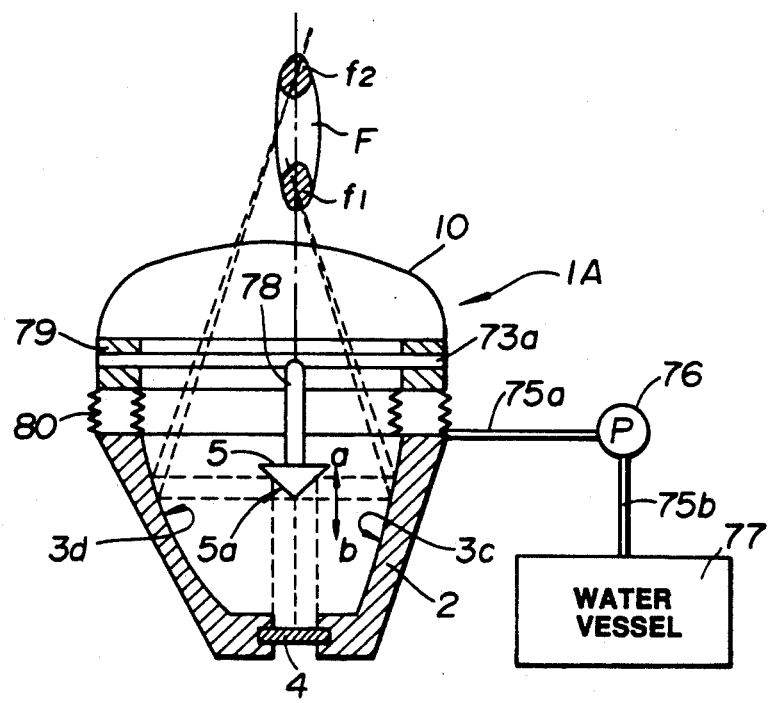
FIG. 17 is an enlarged cross sectional view of an essential part of the cone moving device illustrating its concrete construction in the ultrasonic wave therapeutic device according to the eighth embodiment of the present invention.

FIG. 17 is a schematic constructional diagram of an ultrasonic wave oscillator 1A in the ultrasonic wave therapeutic device according to the eighth embodiment of the present invention. The ultrasonic wave therapeutic device according to this embodiment is constructed in the same way as the therapeutic device of the above described seventh embodiment, except for the cone moving device 28 of the ultrasonic wave therapeutic device 101 in the above described sixth embodiment and the shape of the inner peripheral reflecting surface 3, and therefore the same component has the same number to omit detailed explanation.

In the ultrasonic wave therapeutic device according to the eighth embodiment, the conical reflector 5 having a conical reflecting surface 5a is fixedly supported, with the central position of its bottom surface, by one end of the supporting bar 78, and the other end of the supporting bar 78 is fixed to the supporting member 73a of bar type, which is tightened by the ring 79.

One end surface of the ring 79 is fixed to a bellows 80, which is mounted on the open, end surface of the reflecting case 2, and the other end surface is adhered to the water bag 10. The bellows 80 is connected with the pump 76 through a hose 75a, and the pump 76 is connected with the water vessel 77 through a hose 75b.

The paraboloidal, inner reflecting surface of the reflecting case is so constructed that the right half (in FIG. 17) of a paraboloidal, inner reflecting surface 3c, referring to the central axis of the reflecting case 2, has a geometrical focus $f_1$, and that the left half (in FIG. 17) of a paraboloidal, inner reflecting surface 3d has a geometrical focus $4_s$. In such a construction of this embodiment, each inner reflecting surface of the reflecting case 2 comprises a combination of paraboloidal surface which have such different focuses as $f_1$ and $f_2$.

In the ultrasonic wave therapeutic device of this embodiment having the above described construction, the pump 76 is driven, and water is supplied from the water vessel 77 to the bellows 80 through the hoses 75a and 75b so as to move the conical reflector 5 toward the arrow a. Then, as the bellows 80 is expanded to lift up the ring 79, the conical reflector 5 moves toward the arrow a. On the other hand, if the reflector 5 is to be moved toward the arrow b, pump 76 is made to move reversely so as to suck in water from the bellows 80. Then, as the bellows 80 is folded and compressed, the ring 79 and the conical reflector 5 are moved toward the arrow b.

When the conical reflector 5 is moved to the arrow a or b in the above described manner, the focused condition of ultrasonic waves will be described referring to FIG. 18(A) and FIG. 18(B). As shown in these figures, an ultrasonic wave generated from the ultrasonic wave oscillator 4 is at first reflected by the conical reflecting surface 5a of the conical reflector 5, and then reflected by the inner, peripheral surfaces 3c and 3d of the reflecting case 2 so as to be focused to each of the different focusing areas $F_1$ and $F_2$. The inner, peripheral reflecting surfaces 3c and 3d are constructed with a combination of paraboloids, which have different focuses around their peripheries, so the focusing area of ultrasonic waves becomes F.

Figure 18A:
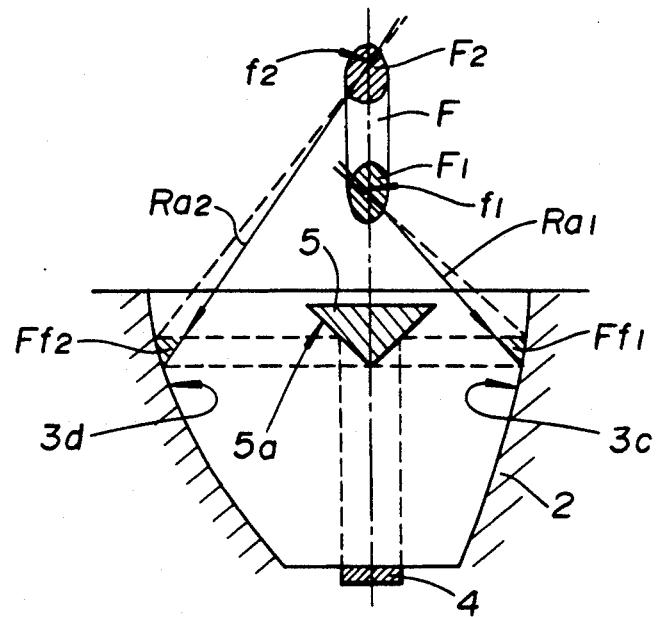
FIG. 18 (A) and (B) are operational diagrams illustrating, respectively, operation of the cone moving device of FIG. 17.
Figure 18B:
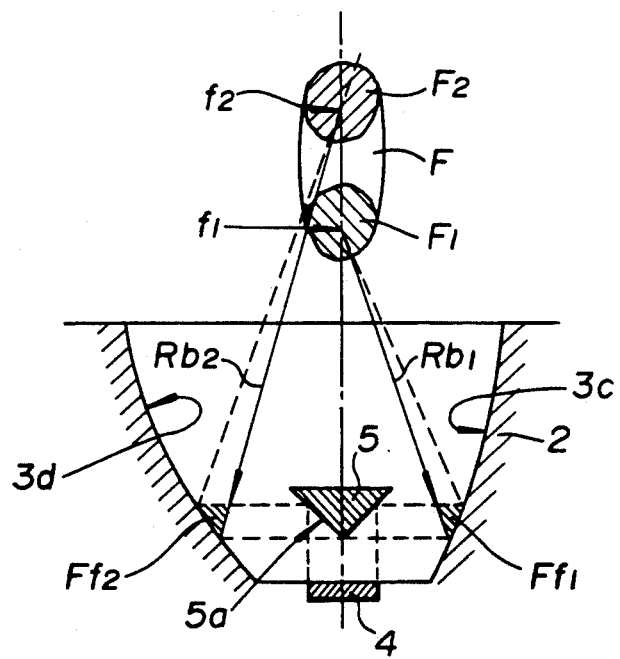

The focusing condition of ultrasonic waves is compared, between FIG. 18(A) and (B). In these figures, when an ultrasonic wave is reflected from the paraboloidal, inner reflecting surfaces 3c and 3d of the reflecting case 2, and when another ultrasonic wave is reflected from the conical reflecting surface 5a of the conical reflector, the crossing areas of these ultrasonic waves are $F_{f1}$ and $F_{f2}$, and distances between the crossing areas $F_{f1}$, $F_{f2}$, and the geometrical focuses $F_1$, $F_2$ of the paraboloidal, inner reflecting surfaces 3c, 3d are $R_{a1}$ and $R_{a2}$, respectively, if the conical reflector 5 is far from the ultrasonic wave oscillator 4 as shown in FIG. 18(A). On the other hand, if the conical reflector 5 is close to the ultrasonic wave oscillator 4 as shown in FIG. 18(B), the distances are $R_{b1}$ and $R_{b2}$, respectively. Then, as is clear from FIG. 18(A) and (B), the following relationship is given:

$$R_{a1} < R_{b1}, R_{a2} < R_{b2}$$

As ultrasonic waves are focused on the focusing area F, it is conveniently considered that some ultrasonic waves are radiated from an ultrasonic wave oscillator of circular shell type having a curvature radius of $R_{a1}$ or $R_{a2}$, and that the other ultrasonic waves are radiated from an ultrasonic wave oscillator of circular shell type having a curvature radius of $R_{b1}$ or $R_{b2}$. In this case, as an ultrasonic wave is focused sharply when the curvature radius of the ultrasonic wave oscillator is small, the ultrasonic wave will be focused sharply when the conical reflector 5 is close to the ultrasonic wave oscillator 4, than when the conical reflector 5 is far from the ultrasonic wave oscillator 4.

In this manner, as the ultrasonic wave therapeutic device of this embodiment has an elongated focusing area, it is particularly advantageous for an elongated object to be treated. And, as the width of a focusing area can be changed only by moving the conical reflector 5 in the longitudinal direction, effective treatment can be given with a simple operation.

It is understood that the paraboloidal, inner reflecting surface of this embodiment can be formed by combining two or more inner-peripheral reflecting surfaces which have, respectively, a different, geometrical focus, as is described in the seventh embodiment.

According to the seventh and eighth embodiments previously described, when the conical reflector having a conical reflecting surface is moved along the central axis of the ultrasonic wave oscillator, an ultrasonic wave heating area can be changed; the medical treatment can be done with simple operation without interruption.

Figure 19:
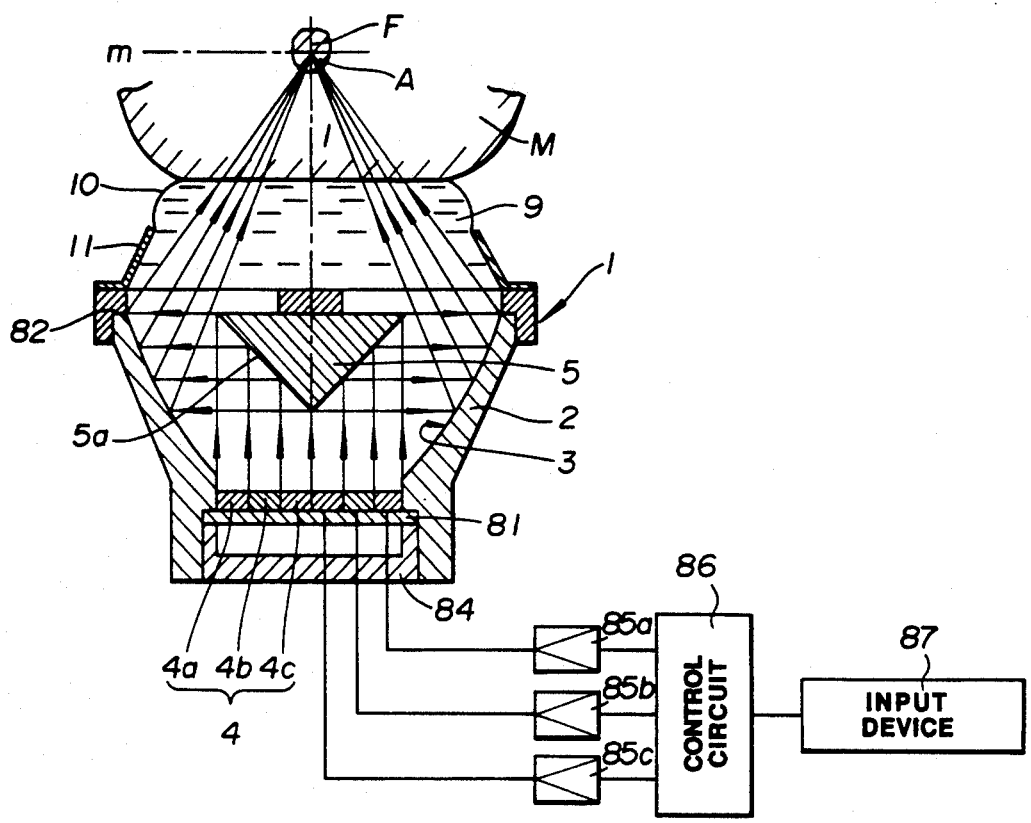
FIG. 19 is constructional diagram of the whole parts of the ultrasonic wave therapeutic device according to the ninth embodiment of the present invention.

FIG. 19 is a schematic diagram illustrating the whole construction of an ultrasonic wave therapeutic device according to the ninth embodiment of the present invention. In this figure, a numeral 1 shows a focused ultrasonic wave oscillator comprising, for example the water bag 10 of soft resin film, in which an ultrasonic wave transmitting medium, for example water is filled. A symbol M shows a human body, and a symbol A shows a position to be treated, for example a tumor A of the human body M. The focused ultrasonic wave oscillator 1 is contacted with the human body M through the water bag 10, corresponding to the position A to be cured.

In the focused ultrasonic wave oscillator 1, a plurality of oscillators 4a to 4c form an ultrasonic wave generator 4 which is driven with the same frequency and is fixed on a supporting disk 81. This oscillator 4 is divided into individual oscillators 4a, 4b and 4c in a circular arrangement around the central axis. On the front surface of the ultrasonic wave oscillator 4, a conical reflector 5 having a conical reflecting surface 5a is arranged around its rotating center axis 1, on which a concave reflecting case having the paraboloidal reflecting surface 3 is also arranged. The paraboloidal, inner reflecting surface 3 of the reflecting case 2 has a rotatively symmetrical axis m, which is crossed with, and perpendicular to the central axis 1. On the open end surface around the circle of the reflecting case 2, a support ring 82 is fixed to support the reflector 5, and, on its upper surface is fixed a film fixing member 83, which connects the water bag 10 with the support ring 82. Moreover, the support member 81 is fixed to the frame of the reflecting case 2 by using a fixing frame 84.

By the way, the divided oscillators 4a, 4b and 4c are electrically connected with amplifiers 85a, 85b and 85c, respectively, and each of these amplifiers 85a, 85b and 85c is connected with a control circuit 87, which switches over generation of a driving signal and its timing. Signals such as the driving timing and power set by the input device 87, are input to the control circuit 86.

In the ultrasonic wave therapeutic device according to the ninth embodiment having the above described construction, at first the focused ultrasonic wave oscillator 1 is, as shown in the figure, arranged in such a way that it contacts the surface of the human body M corresponding to the position A to be treated, through the water bag 10. At that time, ultrasonic waves are set to be focused on the position A to be treated, and, driving power to be input to each of the ultrasonic wave oscillators 4a, 4b and 4c, and the timing to drive each oscillator, are preliminary set by the input device 87. When the oscillators are intended to operate at the same time, the control circuit 87 makes the oscillators transmit signals having the same phase to amplifiers 85a, 85b and 85c, and the amplified signal will drive the oscillators 4a, 4b and 4c. Then, an ultrasonic wave generated from the front end of the oscillators, is transmitted toward the arrow so as to reach the conical reflector 5. After that it is reflected by the conical reflecting surface 5a so as to change its transmitting direction, and reaches the reflecting case 2. The ultrasonic wave is reflected by the paraboloidal, inner reflecting surface 3 of the reflecting case 2, and is focused on the focus F.

Figure 20A:
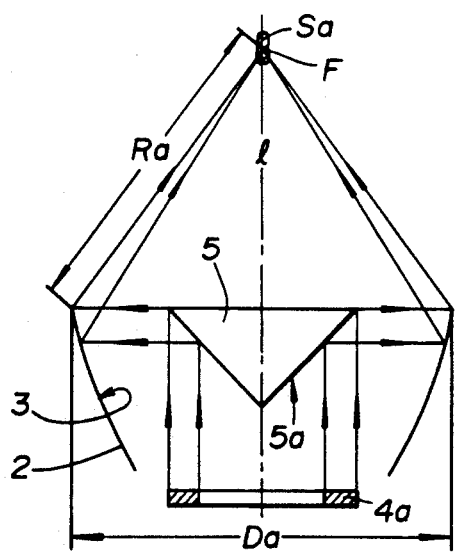
FIG. 20 (A), (B) and (C) illustrate each focusing condition when a focusing condition of an ultrasonic wave is changed in the ninth embodiment of the ultrasonic wave therapeutic device.
Figure 20B:
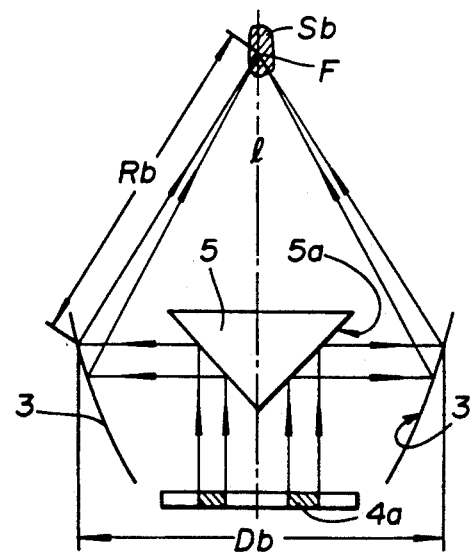
Figure 20C:
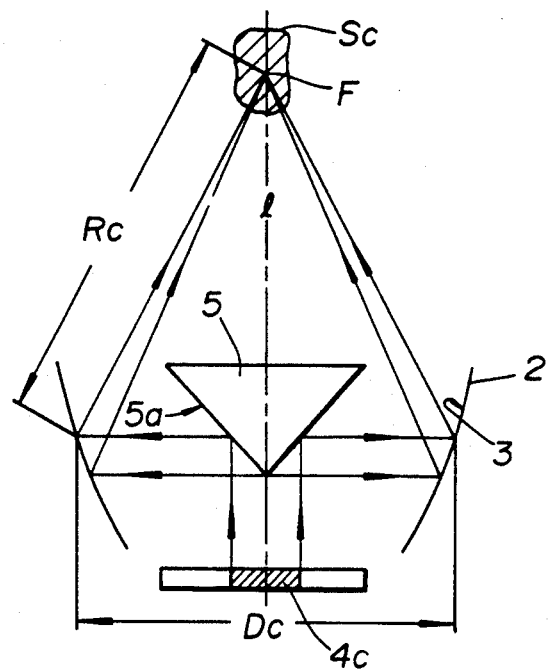

In this manner, an ultrasonic wave is focused for medical treatment. Next will described how to change the ultrasonic wave distribution depending on the size of the position A to be treated at the time of medical treatment, referring to FIG. 20. FIG. 20(A) shows only when the ultrasonic wave oscillator 4a is driven; FIG. 20(B) shows only when the ultrasonic wave oscillator 4b is driven, and FIG. 20(C) shows only when the ultrasonic wave oscillator 4c is driven. In all of these figures, it is indicated that the ultrasonic waves are focused. When the ultrasonic wave generated from the ultrasonic wave oscillator 4 is transmitted and reflected by the reflecting case 2 to be focused on the focus F, and an aperture is indicated by a symbol D, which is the diameter of a circle having a radius that is obtained by connecting the outer point of reflection and the central axis 1, the distance between the outer point of reflection of the reflecting surface 3 and the focus F is indicated by a symbol. In FIG. 20(A), (B) and (C), the aperture diameters are Da, Db and Dc, respectively, and the curvature radii are Ra, Rb and Rc, respectively.

In general, when an ultrasonic wave is focused, it is known that the convergency becomes larger if the diameter of an aperture is smaller. Here, as the aperture diameters are Dc<Db<Da and the curvature radii are Dc>Db>Da, the largest convergency is obtained when driving the outside oscillator 4a in FIG. 20(A), the convergency becomes the smaller convergency when driving the middle oscillator 4b in FIG. 20(B). The convergency becomes the smallest when driving the inside oscillator 4c in FIG. 20 (C). Therefore, when the oscillator 4 is driven with equal energy, the equivalent energy distribution in the vicinity of the focus F becomes Sa, Sb and Sc as shown in the figure; the energy is concentrated to a narrow area when the outside oscillator 4a is driven, and the energy is scattered to a wide area when the inside oscillator 4c is driven.

In this way, if the size of a tumor is small, only the outside oscillator 4a is driven, if a medium size, only the middle oscillator 4b is driven, and, if the size is large, only the inside oscillator 4c is driven, so that the tumor can be heated and treated uniformly.

In the previous description, we have described only driving one of oscillators 4a, 4b and 4c, but two or three oscillators can be driven at the same time if the energy to be irradiated is increased or the condition of distribution should be changed.

In the ultrasonic wave therapeutic device according to the ninth embodiment, two or more ultrasonic wave oscillators are arranged on concentric circles so as to be able to drive any one of them independently, so a focused condition of ultrasonic waves can be changed easily according to the size of a position to be treated, and energy is irradiated uniformly to a wide range, and therefore very high therapeutic effect can be achieved.

Figure 21:
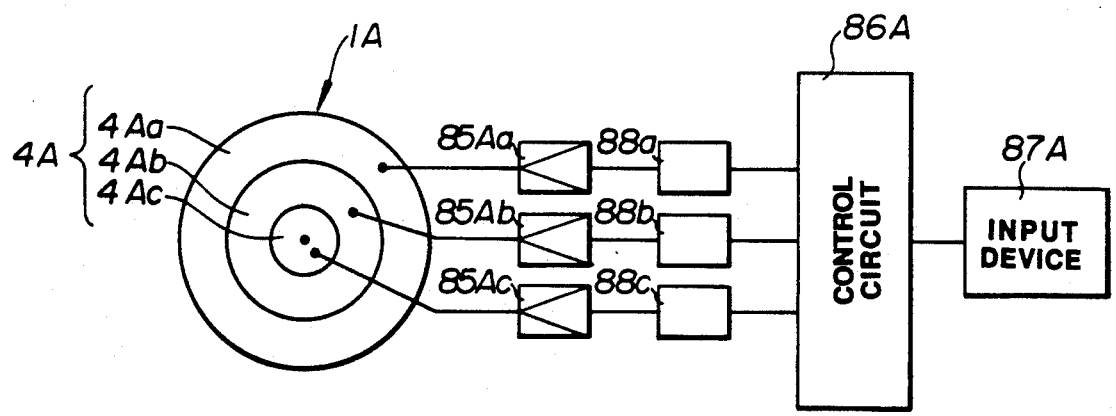
FIG. 21 is a schematic constructional view of an essential part of the ultrasonic therapeutic device according to the tenth embodiment of the present invention.

FIG. 21 is a plan view illustrating the outlined construction of the essential part of the ultrasonic wave therapeutic device according to the tenth embodiment of the present invention. A focused ultrasonic wave oscillator 1A of this embodiment is constructed in approximately the same way as the previously described ninth embodiment; but, only an ultrasonic wave oscillator 4A arranged in the focused ultrasonic wave oscillator 1A and a means to be connected with the oscillator to drive it, have different constructions, so only the constructions and functions of them will be described.

In the figure, the ultrasonic wave oscillator 4A of ring type having a rotational center of the central axis 1, is divided into oscillator components 4Aa, 4Ab and 4Ac, which have different frequencies to be generated, and is electrically connected with oscillators 88a, 88b and 88c through amplifiers 85a, 85b and 85c. Each oscillator is connected with a control circuit 85A, which switches over timing of its driving signal, and a control circuit 87A is supplied with such signals as the driving timing and power, which are set by using an input device 87A. Here, as for the ultrasonic wave oscillator 4A which generates different frequencies, for example the outside oscillator 4A generates an ultrasonic wave of high frequency, 2 MHz, the middle oscillator 4$b$ generates an ultrasonic wave of middle frequency, 1 MHz, and the inside oscillator 4$c$ generates an ultrasonic wave of low frequency, 500 KHz.

In the ultrasonic wave therapeutic device of the tenth embodiment having the above described construction, at first the focused ultrasonic wave oscillator 1A is made to face the human body, and then the oscillator 4A is driven independently according to the size of a position to be treated. In this case, when the position to be treated is small, an operation of the input device 87A makes the control circuit 87A drive only an oscillator 88$a$; a signal amplified by the amplifier 85A$a$ is transmitted to the oscillator 4A$a$; and an ultrasonic wave of high frequency is generated to be converged on the focus. In the same way, when the position to be treated is large, the oscillator 4A$c$ is driven, and when it is middle-sized, the oscillator 4A$b$ is driven.

Frequency of the oscillator 4A increases from inside to outside. This is partly because the convergency is high when the aperture radius is large and the curvature of radius is small, and partly because the convergency becomes higher in an ultrasonic wave of high frequency. This principle is used for medical treatment. Therefore, when the outer oscillator 4A$a$ is driven, energy can be focused uniformly even if a tumor is very small. When the inner oscillator 4A$c$ is driven, the energy can be scattered uniformly to irradiate a tumor of the larger size.

As described in the tenth embodiment, energy can be supplied uniformly to the wider range of a position to be treated; because the ultrasonic wave oscillator 4A is arranged in concentric circles, and some oscillator are used for generating different frequencies.

Figure 22:
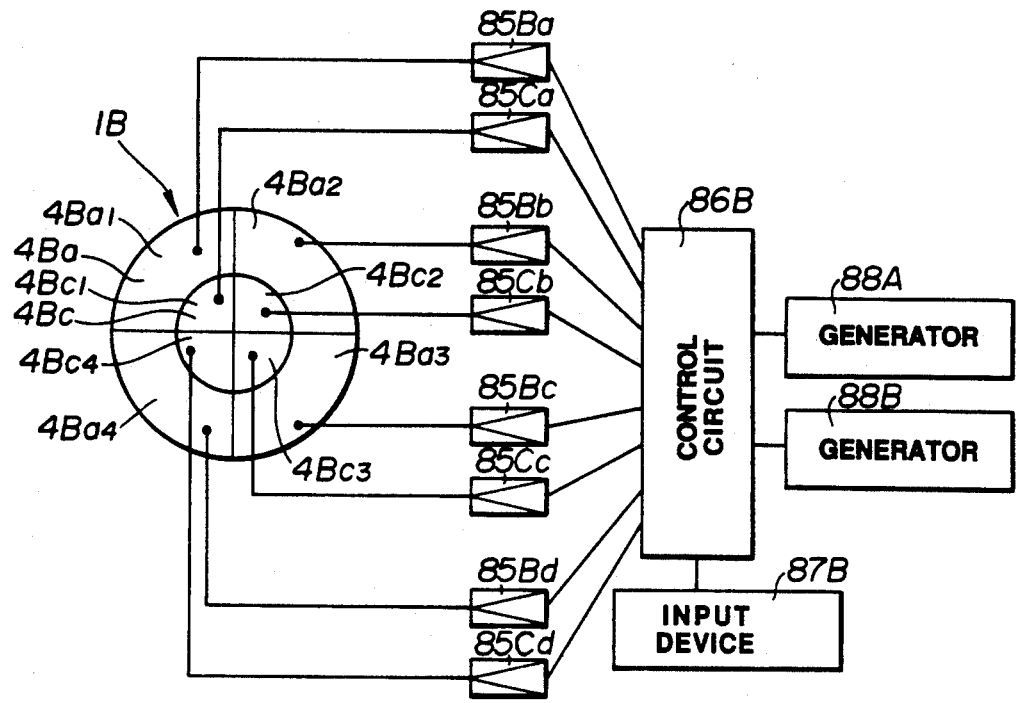
FIG. 22 is a schematic constructional diagram of the ultrasonic wave curing device according to the eleventh embodiment of the present invention.

In the next place, FIG. 22 is a plan view illustrating the outlined construction of an essential part of the ultrasonic wave therapeutic device according to the 11th embodiment of the present invention. A focused ultrasonic wave oscillator 1B according to the 11th embodiment, is constructed in almost the same way as the ninth embodiment, but it is different from the ninth embodiment in that the ultrasonic wave oscillator is divided according to the concentric circle arrangement, and that it is further divided and arranged on lines passing through the center of concentric circles. That is, an outer oscillator 4B$a$ is divided into 4B$a$1. 4B$a$2, 4B$a$3 and 4B$a$4, and, an inner oscillator 4B$c$ is divided into 4B$c$1, 4B$c$2, 4B$c$3 and 4B$c$4. Each oscillator is connected with each of amplifiers 85B$a$-85B$d$, and 85C$a$-85C$d$, and, through a control circuit 86B, the amplifiers 85B$a$-85B$d$ are supplied with a signal generated from an oscillator 88A, and the amplifiers 85C$a$-85C$d$ are supplied with a signal generated from an oscillator 88B. The control circuit 87B is supplied with a signal which is wet by an input device 87 and used for switching the driving timing or diving oscillators. In the same way as the tenth embodiment, the outer oscillators 4B$a$1-4B$a$4 generate an ultrasonic wave of high frequency, for example 2 MHz, and the inner oscillators 4B$c$1-4B$c$4 generate an ultrasonic wave of low frequency, for example 500 KHz.

In the ultrasonic wave therapeutic device having the above described construction according to the eleventh embodiment, at first the focused ultrasonic wave oscillator 1B is arranged opposite to the human body, and then the oscillator is driven. At that time, if the lungs, a bone and any other obstacle exist in the transmitting path of ultrasonic waves, some of eight divided oscillators are driven not to irradiate the obstacles on the transmitting path of ultrasonic waves. That is, when an obstacle can exist on the transmitting path of ultrasonic waves, which are generated from the oscillators 4B$a$1, 4B$c$1, 4B$a$4 and 4B$c$4, an input device 87B is operated so that a signal of high frequency generated from the oscillator 87 is controlled by the control circuit 87B to select its suitable transmitting path if a position to be treated is small, and, only the oscillators 4B$a$2 and 4B$a$3 are controlled through amplifiers 85B$b$ and 85B$c$. On the other hand, when a position to be treated is large, only the oscillator 88B is used for generating a signal of low frequency and for driving only the oscillators 4B$c$2 and 4B$c$3.

In this eleventh embodiment, an oscillator is divided into two or more oscillating elements to drive some of them selectively, and an ultrasonic wave cannot irradiate an obstacle on its transmitting path, and therefore medical treatment can be given safely.

In the previously described manner according to the ninth, tenth and eleventh embodiments, many types of tumors can be treated, and energy can be radiated to a wide range by using a very simple construction so as to give safe and effective medical treatment.

Figure 23:
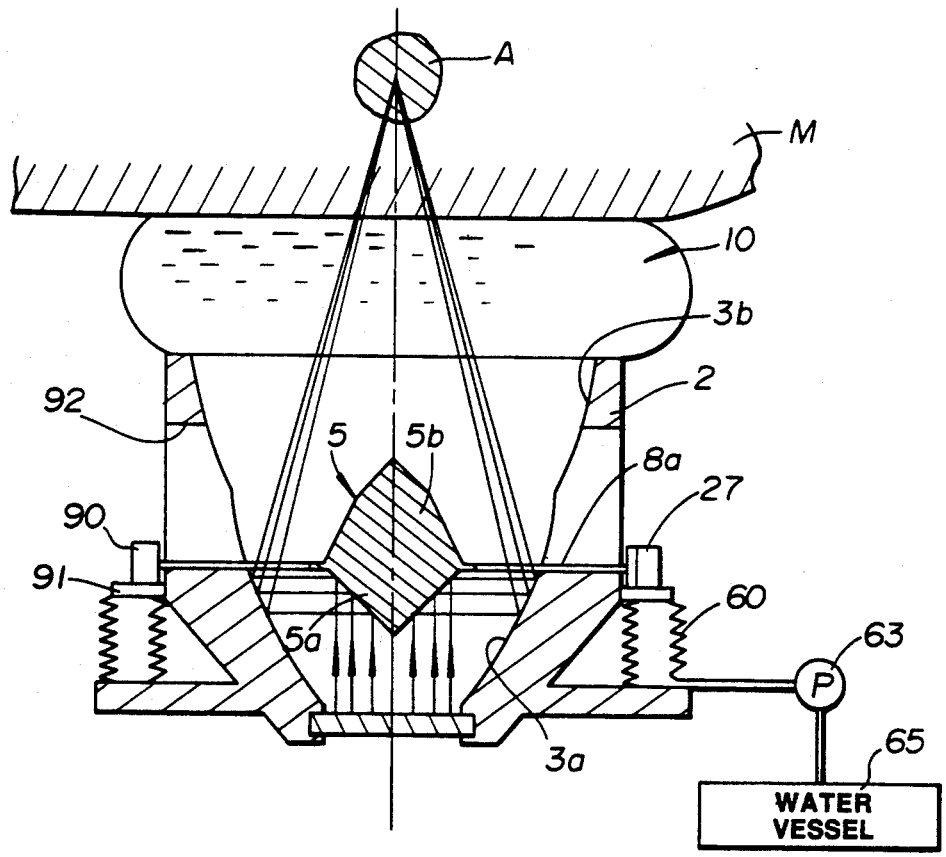
FIG. 23 and FIG. 24 show the twelveth embodiment of the present invention.
Figure 24A:
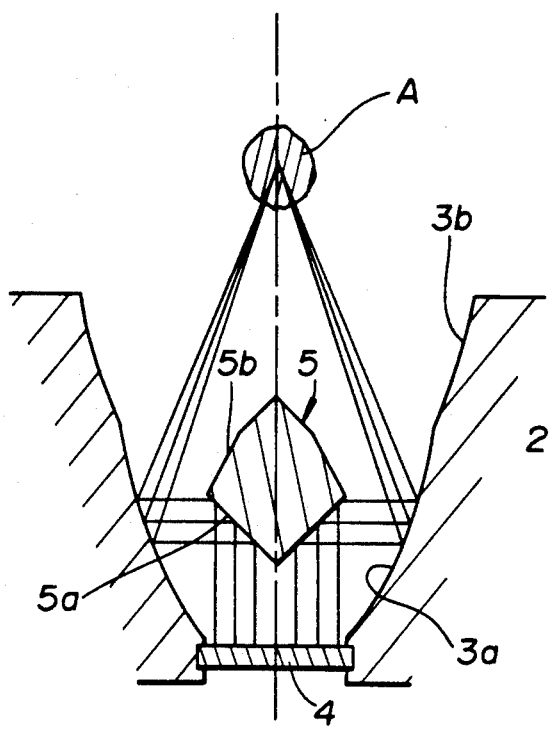
Figure 24B:
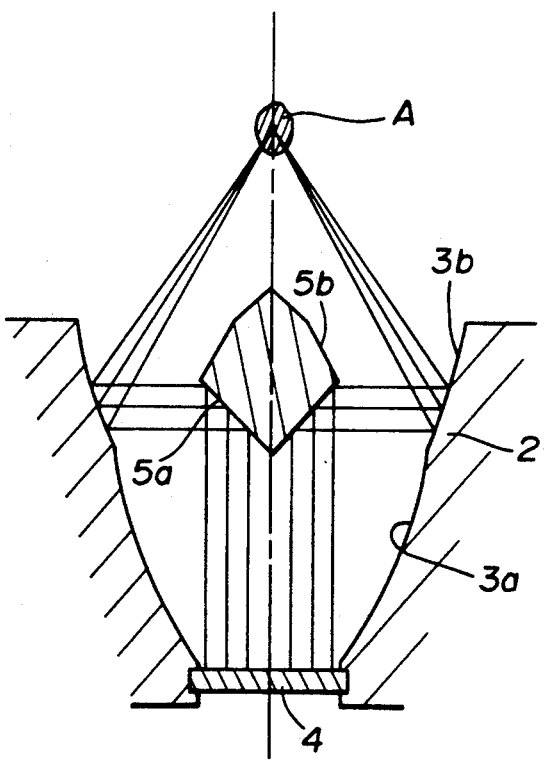
Figure 24C:
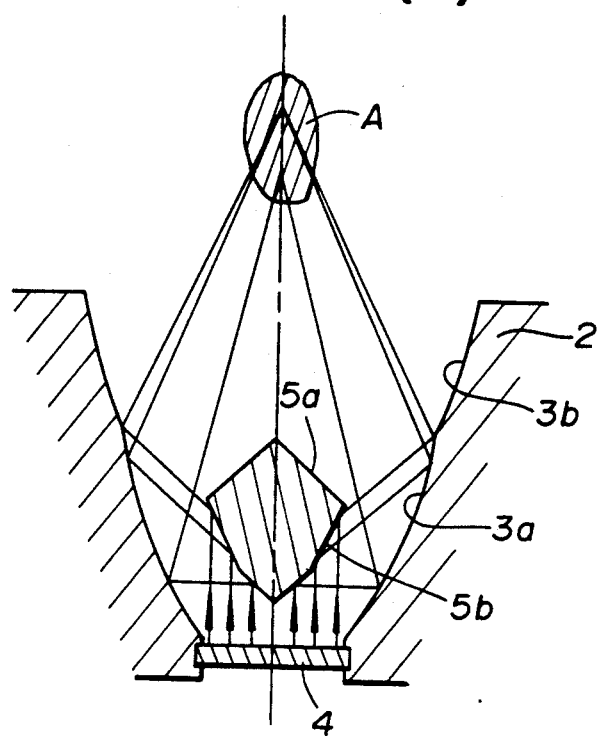
Figure 24D:
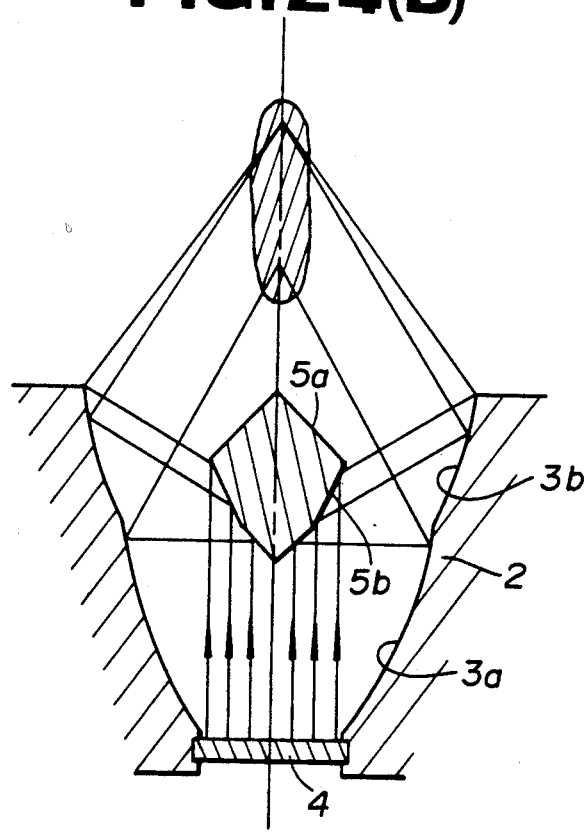

FIG. 23 shows a schematic constructional diagram of an ultrasonic wave therapeutic device according to the 12th embodiment of the present invention. FIG. 24(A), (B), (C) and (D) show focusing conditions of ultrasonic waves. In this embodiment, a reflector 5 having the first and second conical reflecting surfaces 5$a$ and 5$b$ is mounted on a cone fixing bar 8$a$, and is rotated through the bar 8$a$ by using the stepping motor 27; so, the first and second conical reflecting surfaces 5$a$ and 5$b$ can be selectively switched over, as is shown in the fourth embodiment. In addition to this, the reflector 5 can be moved close to, or far from the ultrasonic wave focusing point (upward and downward directions in the figure), and therefore the paraboloidal, inner reflecting surface 3 of the reflecting case 2 is formed with a first reflecting surface 3$a$ and a second reflecting surface 3$b$, both of which have a different reflecting angle. In this manner, a bearing 90 of the motor 27 and the bar 8$a$ is placed on the top of a bellows 60 through a stand 91, and is moved upward and downward according to expansion and compression of the bellows 60. Together with this, the reflector 5 which is fixed to the bar 8$a$, is moved between the first reflecting surface 3$a$ and the second reflecting surface 3$b$. In the range of upward and downward movements of the bar 8$a$, a guide groove 92 is formed on the reflecting case 2. The bellows 60 can be expanded and compressed by charging and discharging a liquid or gas using a pump 63, and, in the case of a liquid, a tank 65 is connected to the pump 63. In such a construction, the reflector 5 is made to rotate and move in the upward and downward directions, so a focusing area of ultrasonic waves can be changed in various ways as shown in FIG. 24(A) to (D).

Figure 25A:
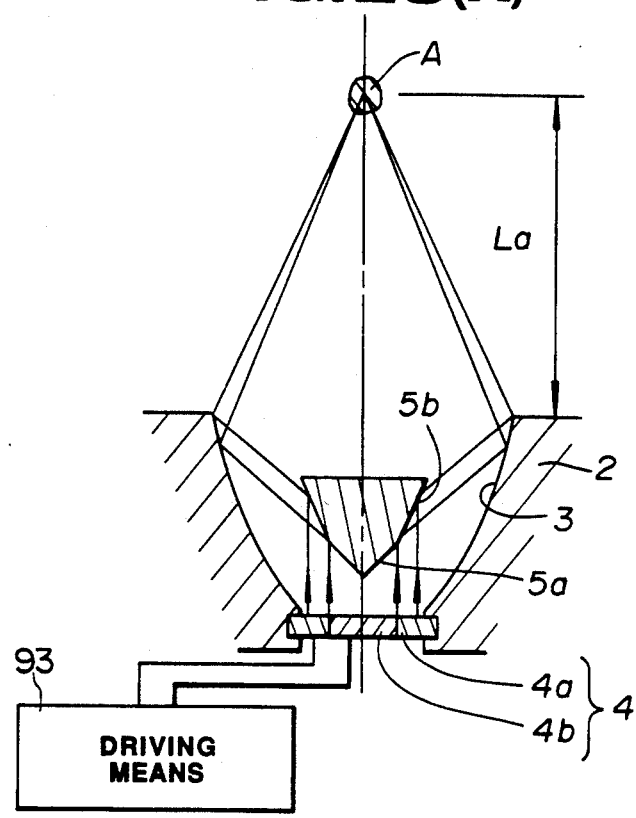
FIG. 25 (A) and (B) show the thirteenth embodiment of the present invention.
Figure 25B:
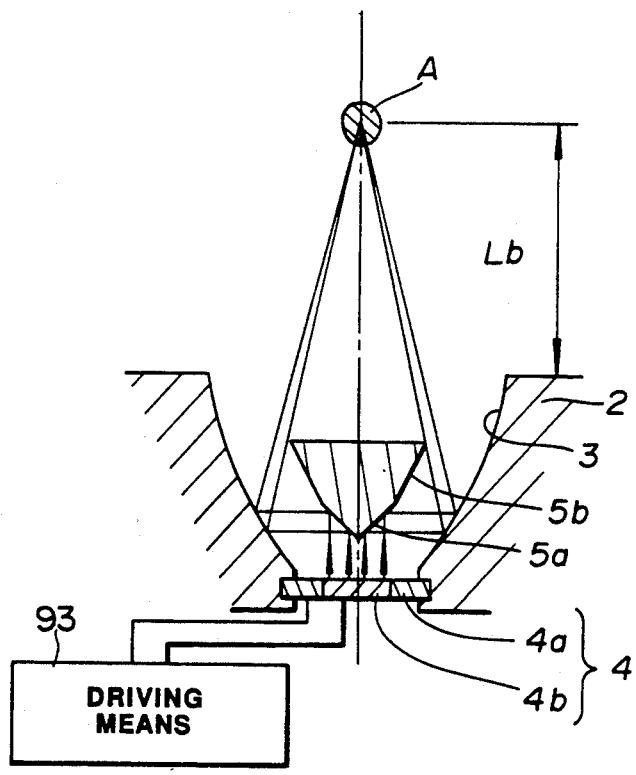

FIG. 25 shows the 13th embodiment of the present invention. This embodiment is constructed with a conical reflector 5 having a plurality of reflecting surfaces of different top angles for example, a first reflecting surface 5$a$ and a second reflecting surface 5$b$, an oscillator 38 divided into, for example first and second oscillators 4a and 4b which are arranged in concentric circles; and a selective, driving means for driving the oscillator 4 selectively are provided. In this case, each of the divided first and second oscillators 4a and 4b is opposite to each of the first and second reflecting surfaces 5a and 5b having a different top angle. In such a construction, when the oscillators 4a and 4b are switched over and driven, the focusing distance of ultrasonic waves can be changed as shown in FIG. 25(A) and (B). The focusing distance La in FIG. 25(A) and the focusing distance Lb in FIG. 25(B) have relationship, La>Lb. In this construction, the ultrasonic wave oscillator is small, and a focusing distance of ultrasonic waves can be changed only by switching over an oscillator to be driven.

Figure 26A:
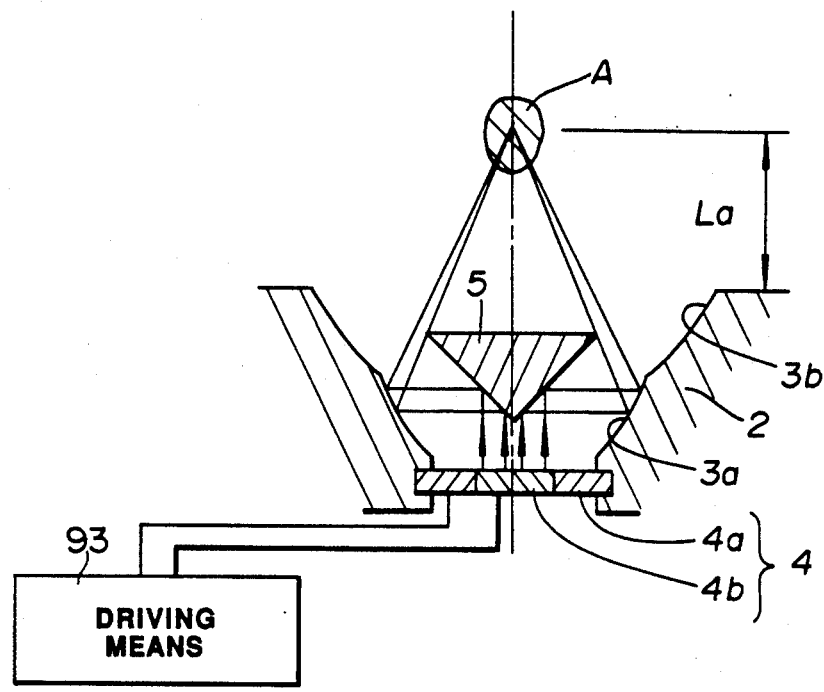
FIG. 26 (A) and (B) show the fourteenth embodiment of the present invention.
Figure 26B:
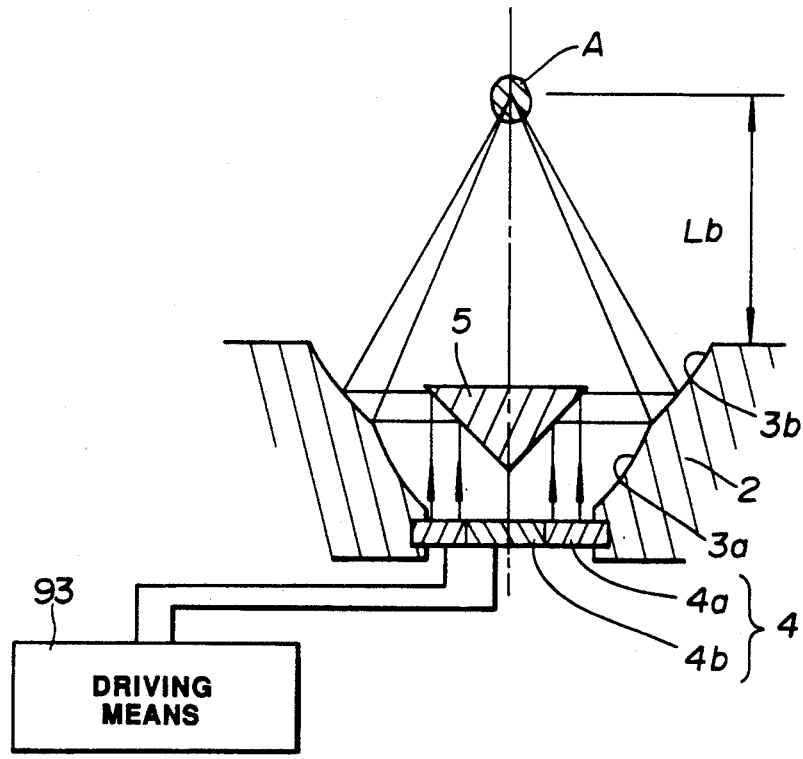

FIG. 26 shows the 14th embodiment of the present invention. This embodiment is constructed with a reflecting case 2 having a first, paraboloidal reflecting surface 3a and a second, paraboloidal reflecting surface 3b; first and second oscillator 4a, 4b arranged in concentric circles, a selective driving means for driving the oscillator selectively. Each of the reflecting surfaces 3a and 3b is facing each of the oscillators 4a and 4b. The operation and effects of this embodiment is the same as those of the above described thirteenth embodiment.

Figure 27:
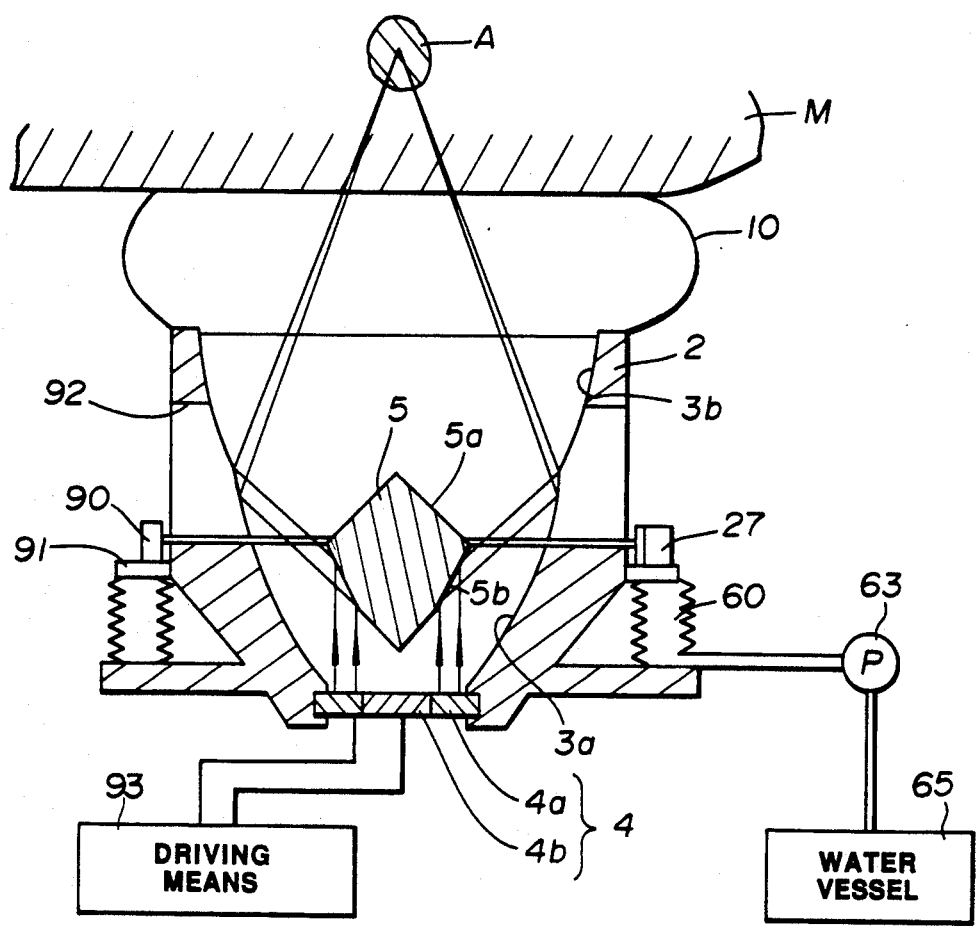
FIG. 27 shows the fifteenth embodiment of the present invention.

FIG. 27 is a schematic diagram illustrating the fifteenth embodiment of the present invention. This embodiment is different from the twelfth embodiment (refer to FIG. 23) in that the ultrasonic wave oscillator 4 is divided into, for example two oscillators, a first one 4a and a second one 4b, and a selective driving means 93 is provided for driving these oscillators selectively. Thus, as described in relation to FIG. 28(A)–(D), the focusing distance can be changed as La, Lb, Lc and Ld, the focusing distance and the condition can be finely adjusted, and therefore a suitable irradiating pattern can be obtained for medical treatment.

Figure 29:
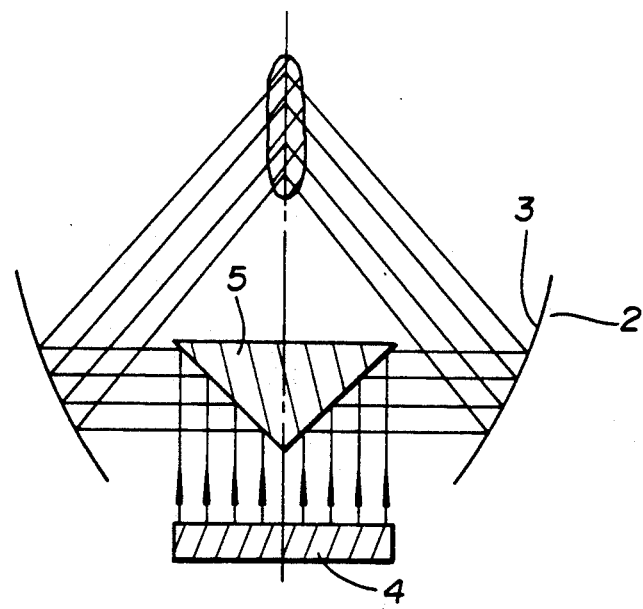
FIG. 29 shows the sixteenth embodiment of the present invention.
Figure 28A:
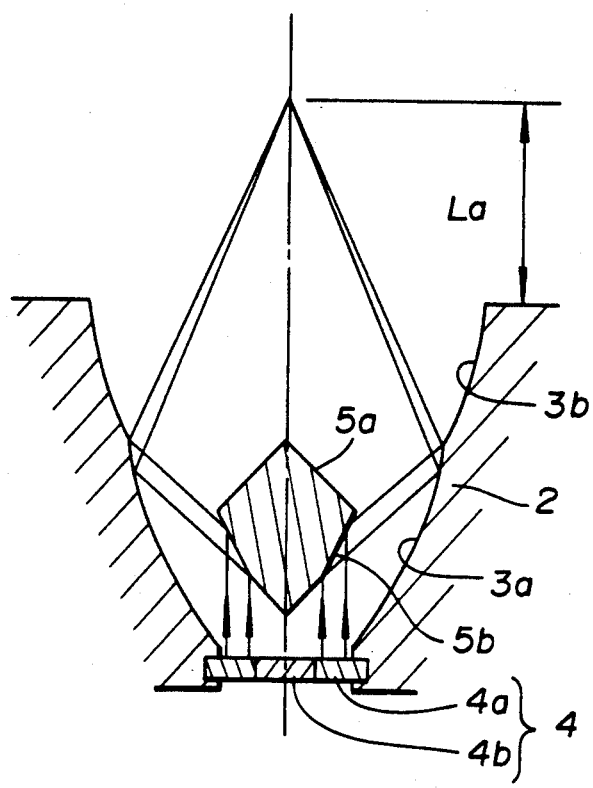
FIG. 28 (A) to (D) are diagrams illustrating the fifteenth embodiment of the present invention.
Figure 28B:
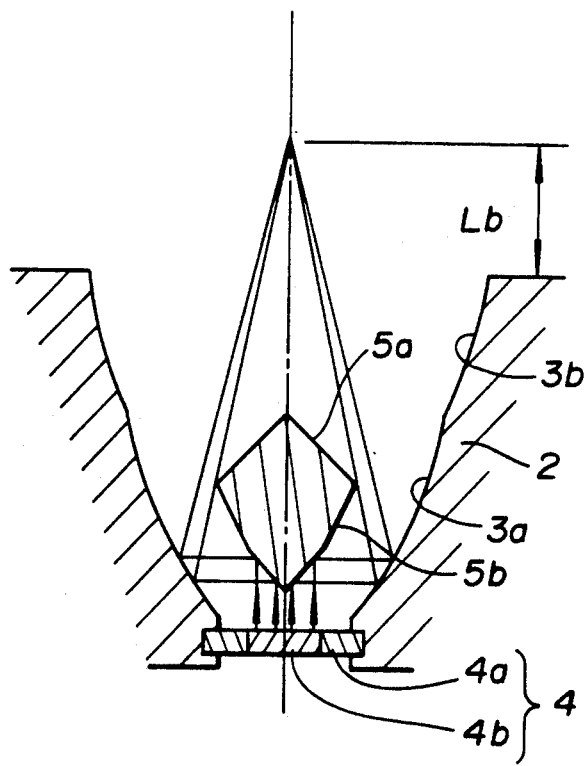
Figure 28C:
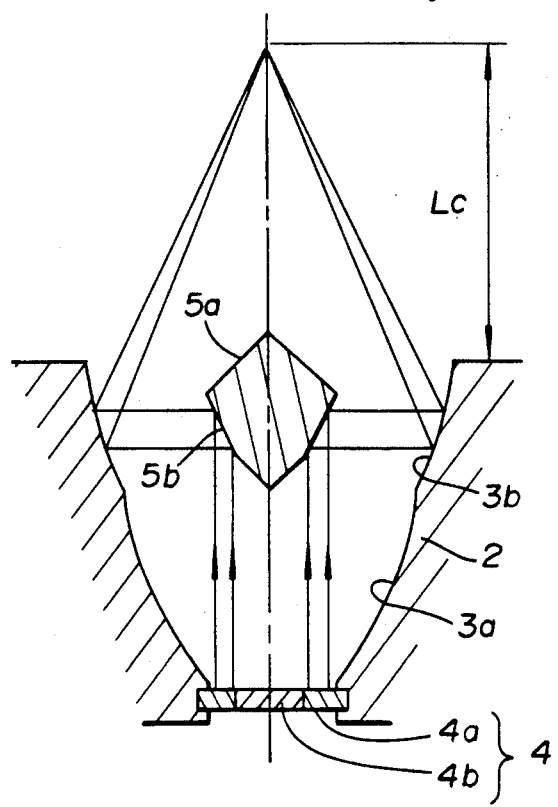
Figure 28D:
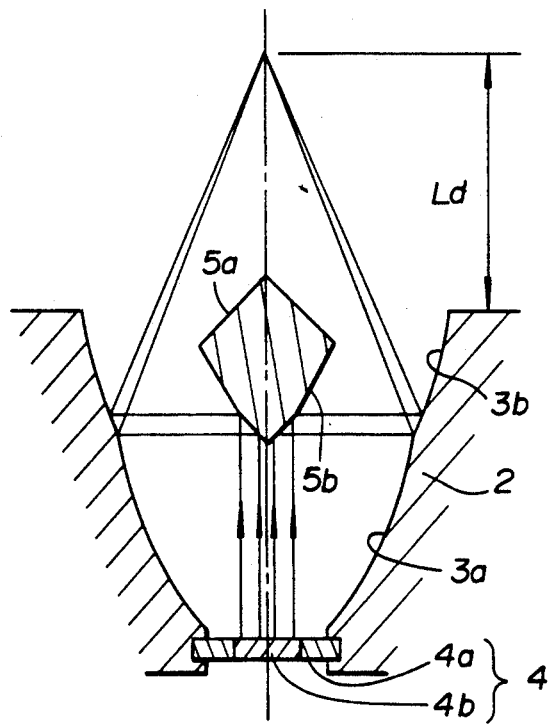

FIG. 29 shows the sixteenth embodiment of the present invention. In this embodiment the paraboloidal, inner reflecting surface 3 of the concave reflecting case 2 is represented with an approximate formula having a plurality of focuses, and has a form which is obtained by rotating the formula around the central axis. In such a construction, an ultrasonic wave can be focused on a predetermined range of length, so it is advantageous that an ultrasonic wave can be irradiated in the longitudinal direction.

Figure 30:
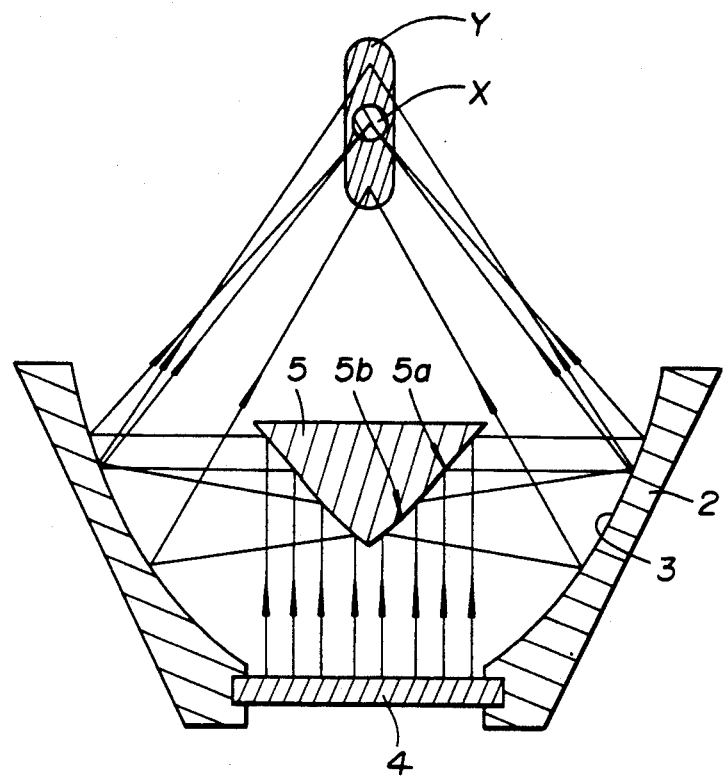
FIG. 30 and FIG. 31 show the seventeenth and eighteenth embodiments of the present invention.

FIG. 30 shows the 17th embodiment of present invention, and this forms a plane 5c and a bended surface 5d on the conical reflector 5. In this embodiment, an ultrasonic wave reflected from the plane 5c of the reflector 5 is focused on an area X, and an ultrasonic wave reflected from the bent surface 5d is focused on an area Y. In such a construction, as the functioning area of ultrasonic waves can be strengthened or weakened (the area X is strengthened, and the area Y is weakened), a portion to be added with strengthened ultrasonic waves, can be distinguished from another portion to be added with weakened ultrasonic waves. For example, a strong ultrasonic wave irradiates a portion of large tumor, and a weak ultrasonic wave irradiates the peripheral, small tumors, and therefore a wide range of medical treatment can be given at one time.

Figure 31:
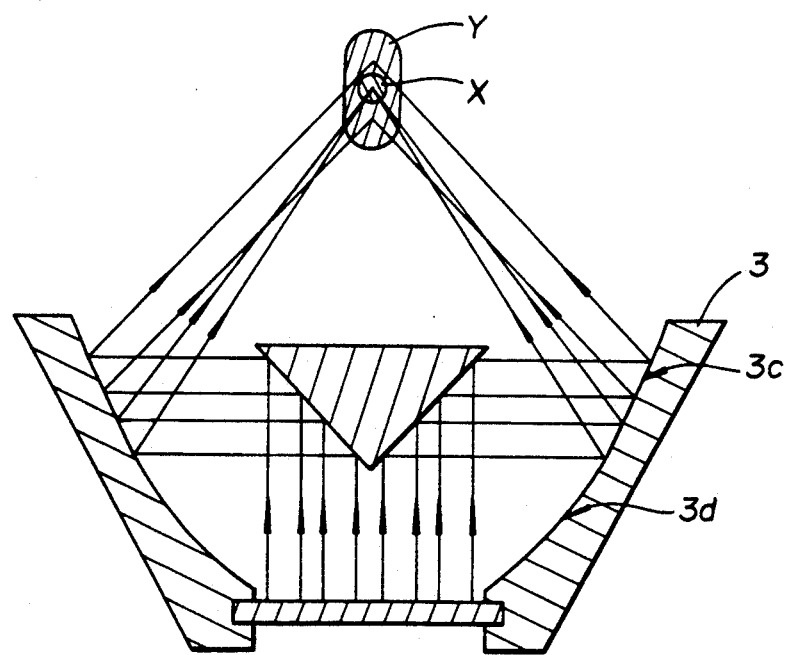

FIG. 31 shows the 18th embodiment of the present invention, which forms a plane 3c and a bent surface 3d on the reflecting surface of the concave, reflecting case 2; and, an ultrasonic wave reflected from the plane 3c is collected to the area Y, and an ultrasonic wave reflected from the bent surface 3d is collected to the area X (this is the reverse of the 17th embodiment). Functions of the 18th embodiment is the same as those of the 17th embodiment.

Figure 32A:
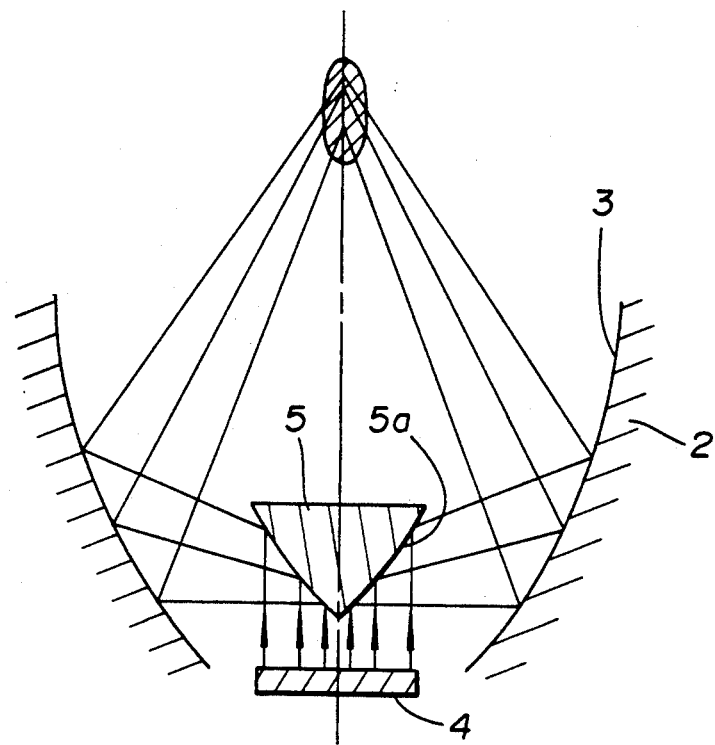
FIG. 32 (A) and (B) show the nineteenth embodiment of the present invention.
Figure 32B:
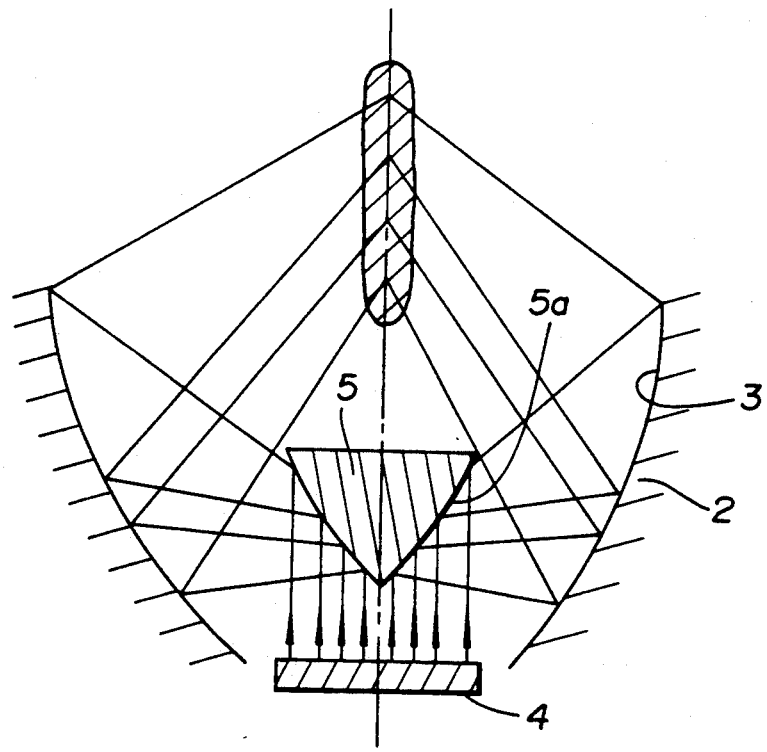

FIG. 32 shows the 19th embodiment of the present invention, comprising a conical reflector 5 having a plurality of reflecting surfaces 5a of different top angle. These reflecting surfaces have, for example a form of a circle rotated around the central axis of a cone. FIG. 32(A) shows when the radius of the circle is large, and (B) shows when the radius of the circle is small, so in this case, an ultrasonic wave is converged to a rectangular portion compared with (A). In this way, by changing the curvature of the reflecting surfaces 5a of the reflector 5, a focused condition of ultrasonic waves can be changed.

Figure 33:
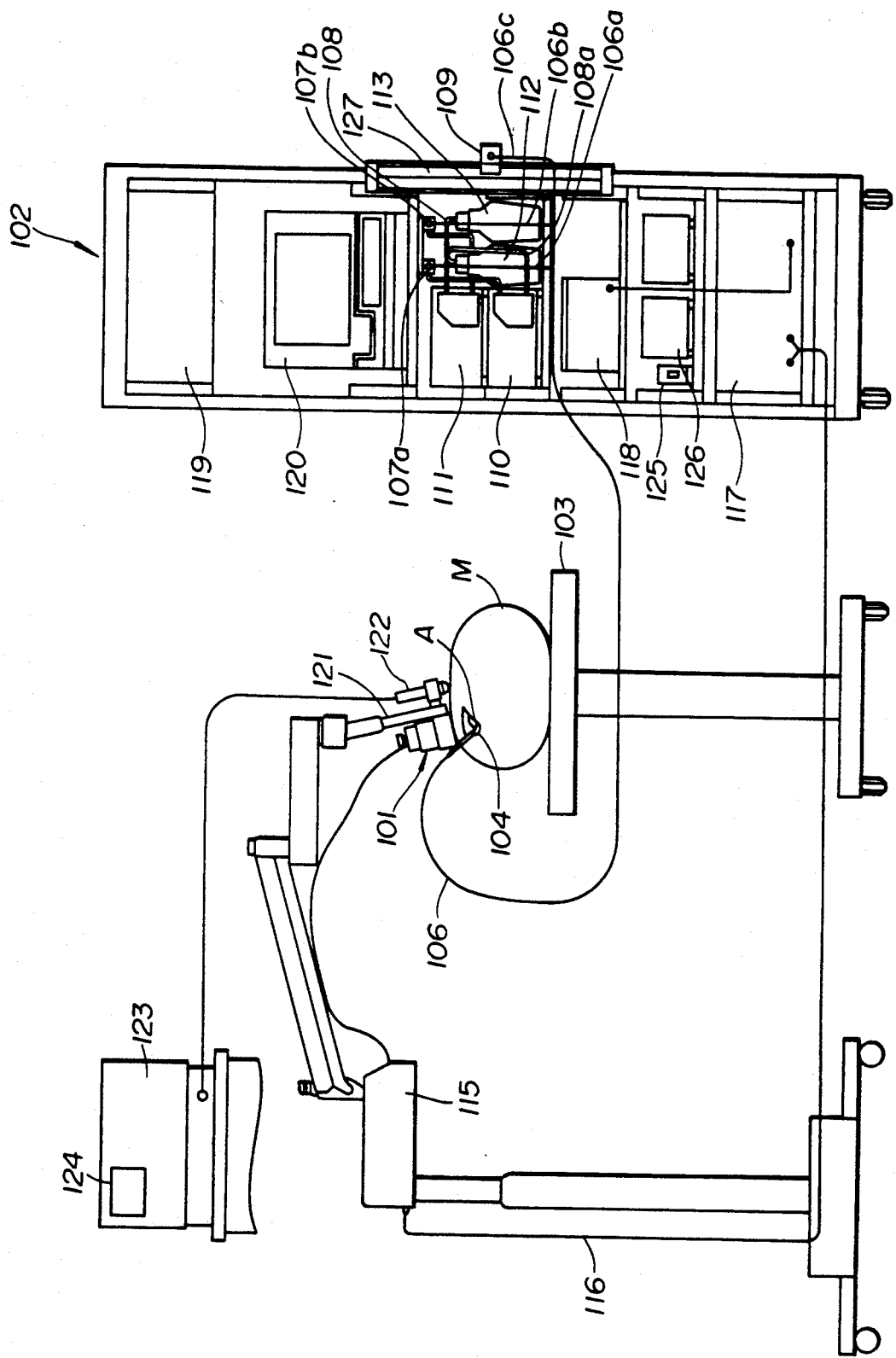
FIG. 33 shows the ultrasonic wave therapeutic device according to the present invention when it is used for calculus melting and curing device.

The previously described, ultrasonic wave curing device according to the present invention, can be used for a calculus melting, treating device for example, as shown in FIG. 33.

In this figure, the human body M is placed on a bed for medical treatment 103 in order to be cured by using the calculus melting, treating device 102. A calculus (gallstone) occurs in the gall 104 of the human body M to be treated. The front end of a catheter 105 is inserted toward the gall 104. The catheter 105 is formed with a porous tube having three lumens, injecting lumen 106a, sucking lumen 106b and pressure lumen 106c. And, three lumens of the catheter 106 are branched at the rear end of the catheter, the injecting lumen 106a is connected with an injecting pump tube 108a through a connector 107a, the sucking lumen 106b is connected with a sucking pump tube 108b through a connector 107b. The pressure lumen 106c is connected with a pressure sensor 109, directly. On the middle portion of the injecting pump tube 108a is arranged an injecting pump 110, and, the other end of the injecting pump tube 108a far from the connector 107a, is connected with a liquid vessel 112, in which a calculus melting solution, for example MTBE is included. On the middle portion of the sucking pump tube 108b is arranged a sucking pump 111, and, the other end of the sucking pump tube 108b far from the connector 107b, is connected with a waste liquid vessel to collect a liquid from the position to be treated. Moreover, the injecting pump 110 and the sucking pump 111 are connected with an input control device 10 through a control unit 119, by which the rotation of each pump 110 or 111 can be set freely. Together with this, the input control device 120 sets driving time and switching operation of each pump 110 or 111, and according to such setting, the pump 110 and 111 are operated.

The ultrasonic wave therapeutic device 101 is provided opposite to the human body M. The ultrasonic wave therapeutic device is fixedly supported by using, for example a supporting member 121, which is provided on the front end of a supporting arm 115. The ultrasonic wave therapeutic device 101 is connected with an amplifier 117 through an electric cable 116, and the amplifier 117 is connected with an oscillator 118. Furthermore, the oscillator 118 is connected with the input control device 120 through the control unit 119. A signal is output from the oscillator 118 depending on the number of pulses, pulse width and driving time which are set by the input control device 120, and amplified by the amplifier 117, thus an ultrasonic wave is generated from the ultrasonic wave therapeutic device 101. The ultrasonic wave will irradiate a portion near the calculus A in the gall 104 of the human body M. An observing, ultrasonic wave probe 122 is removably supported on the supporting member 121 in such a way that it has a symmetrical position relating to the central axis of the supporting member 121. Here, if the observing, ultrasonic wave probe 122 and the ultrasonic wave therapeutic device 101 are turned by 180° on the center of the supporting member 121, the central axis of the ultrasonic wave probe 122 for observation will coincide with that of the ultrasonic wave irradiating area. The observing ultrasonic wave probe 122 is connected with an ultrasonic wave observing device 23, and an ultrasonic wave image including the gall 104 of the human body M, is displayed on a monitor 124.

A power supply switch 125 is connected with the power supply, and it is also connected, through an insulating transformer 126, with the injection pump 110, sucking pump 111, amplifier 117, oscillator 118, control unit 119 and input control device 120. When the switch 125 is turned on, the power is supplied to the injection pump 110, sucking pump 111, amplifier 117, oscillator 118, control unit 119 and input control device 120.

The previously described, pressure sensor 109 is mounted on a rail 127, and can be moved upward and downward freely on the rail 127, thus it can be fixed to any portion on the rail 127.

The present invention is not limited to such particular embodiments as have been described previously. It is understood that this invention can be modified in wide ranges and in various kinds of embodiments within its scope and principle, which will be described in the attached claims.

What is claimed is:

1. An ultrasonic wave therapeutic device, comprising:
    an ultrasonic wave oscillator for generating and radiating an ultrasonic wave;
    a wave radiating surface for radiating said ultrasonic waves generated by said ultrasonic wave oscillator, wherein said wave radiating surface radiates waves along a path substantially in a first direction;
    means for forming at least two focal points of said ultrasonic waves positioned in the path of the radiated ultrasonic waves, said means for forming at least two focal points comprising a surface of a conical reflector, said conical reflector positioned in said first direction from said wave radiating surface, a primary axis extending in said first direction through said wave radiating surface and said conical reflector, said conical reflector for reflecting said ultrasonic waves away from said primary axis;
    wherein the surface of said conical reflector is positioned at an angle with respect to said primary axis such that said ultrasonic waves reflected from said conical reflector are thereby reflected at an angle with respect to said primary axis; and
    a conical reflecting case arranged around the periphery of said conical reflector for reflecting said ultrasonic waves reflected at an angle from said conical reflector.

2. The ultrasonic wave therapeutic device of claim 1, wherein the surface of said means for forming comprises at least two reflecting surfaces on said conical reflector positioned at different angles with respect to said primary axis such that said ultrasonic waves reflected from said at least two reflecting surfaces are thereby reflected at least two different angles with respect to said primary axis and are subsequently reflected by said conical reflecting case to form said at least two focal points.

3. The ultrasonic wave therapeutic device of claim 2, wherein said at least two reflecting surfaces comprise three reflecting surfaces at three different angles with respect to said primary axis so as to reflect said ultrasonic waves at three angles with respect to said primary axis, such that three focal points are formed.

4. The ultrasonic wave therapeutic device of claim 2, wherein said at least two reflecting surfaces are on opposite sides of said primary axis.

5. The ultrasonic wave therapeutic device of claim 2, wherein said at least two reflecting surfaces comprise first and second reflecting surfaces, said first reflecting surface disposed further from said ultrasonic wave radiating surface in said first direction and forming an angle with said primary axis greater than the angle formed between said second reflecting surface and said primary axis.

6. The ultrasonic wave therapeutic device of claim 1, wherein said conical reflector is removably disposed within said ultrasonic therapeutic wave device.

7. The ultrasonic wave therapeutic device of claim 1, wherein a cross section of said conical reflector taken perpendicularly to said primary axis is a circle.

8. The ultrasonic wave therapeutic device of claim 1, wherein said conical reflecting case comprises a parabolic reflecting surface.

9. The ultrasonic wave therapeutic device of claim 1, wherein said conical reflector is connected to a cone fixing bar fixed to an upper portion of said conical reflecting case.

10. The ultrasonic wave therapeutic device of claim 1, further comprising an ultrasonic wave observing probe means for observing an area proximate to said at least two focal points.

11. The ultrasonic wave therapeutic device of claim 1, further comprising a lateral moving means for moving said curing device in directions substantially perpendicular to said primary axis.

* * * * *